United States Patent
Schwartz et al.

(10) Patent No.: US 10,828,106 B2
(45) Date of Patent: Nov. 10, 2020

(54) FIDUCIAL MARKING FOR IMAGE-ELECTROMAGNETIC FIELD REGISTRATION

(71) Applicant: Navix International Limited, Tortola (VG)

(72) Inventors: Yitzhack Schwartz, Haifa (IL); Zalman Ibragimov, Rehovot (IL); Yehonatan Ben David, Tel-Aviv (IL)

(73) Assignee: Navix International Limited, Road Town (VG)

( * ) Notice: Subject to any disclaimer, the term of this patent is extended or adjusted under 35 U.S.C. 154(b) by 385 days.

(21) Appl. No.: 15/569,419

(22) PCT Filed: May 11, 2016

(86) PCT No.: PCT/IB2016/052692
§ 371 (c)(1),
(2) Date: Oct. 26, 2017

(87) PCT Pub. No.: WO2016/181320
PCT Pub. Date: Nov. 17, 2016

(65) Prior Publication Data
US 2018/0296277 A1    Oct. 18, 2018

Related U.S. Application Data

(60) Provisional application No. 62/304,455, filed on Mar. 7, 2016, provisional application No. 62/291,065, filed
(Continued)

(51) Int. Cl.
*A61B 34/10* (2016.01)
*A61B 5/06* (2006.01)
(Continued)

(52) U.S. Cl.
CPC ............ *A61B 34/10* (2016.02); *A61B 5/0538* (2013.01); *A61B 5/063* (2013.01);
(Continued)

(58) Field of Classification Search
CPC .. A61B 34/20; A61B 5/06; A61B 5/05; A61B 5/053; A61B 5/055; A61B 5/0561; A61B 5/063
See application file for complete search history.

(56) References Cited

U.S. PATENT DOCUMENTS

| 4,917,097 A | 4/1990 | Proudian et al. |
| 5,553,611 A | 9/1996 | Budd et al. |

(Continued)

FOREIGN PATENT DOCUMENTS

| EP | 1504713 | 2/2005 |
| EP | 1726268 | 11/2006 |

(Continued)

OTHER PUBLICATIONS

Communication Relating to the Results of the Partial International Search dated Aug. 22, 2016 From the International Searching Authority Re. Application No. PCT/IB2016/052686.
(Continued)

*Primary Examiner* — Eric F Winakur

(57) ABSTRACT

Methods and systems for placement of and/or placement planning for body surface electrodes are described. In some embodiments, body surface electrodes are used to generate intra-body electromagnetic fields sensed by intra-body probes for applications such as electrical field-guided catheter navigation and/or dielectric property-based tissue lesion assessment. Sizes and/or positions of body surface electrodes are optionally selected based on the results of electromagnetic simulations. Criteria for selection include, for example, potential gradient uniformity and/or intensity. In
(Continued)

some embodiments, body surface electrode placement is performed under automated optical guidance. For example, images are obtained and used to indicate and/or assess body surface electrode placement. Optionally, indication is with respect to fiducial marks placed on the body, to which an electromagnetic simulation is spatially registered.

17 Claims, 13 Drawing Sheets

Related U.S. Application Data on Feb. 4, 2016, provisional application No. 62/160,080, filed on May 12, 2015.

(51) Int. Cl.

| | | |
|---|---|---|
| *A61B 5/053* | (2006.01) | |
| *A61B 18/14* | (2006.01) | |
| *A61B 90/00* | (2016.01) | |
| *A61B 34/20* | (2016.01) | |
| *G16H 50/50* | (2018.01) | |
| *G16H 10/60* | (2018.01) | |
| *G16H 30/20* | (2018.01) | |
| *A61B 18/00* | (2006.01) | |
| *A61B 17/00* | (2006.01) | |
| *A61M 25/01* | (2006.01) | |

(52) U.S. Cl.
CPC .......... *A61B 18/1492* (2013.01); *A61B 34/20* (2016.02); *A61B 90/37* (2016.02); *G16H 10/60* (2018.01); *G16H 30/20* (2018.01); *G16H 50/50* (2018.01); *A61B 90/39* (2016.02); *A61B 2017/00026* (2013.01); *A61B 2018/00357* (2013.01); *A61B 2018/00577* (2013.01); *A61B 2018/00642* (2013.01); *A61B 2018/00702* (2013.01); *A61B 2018/00738* (2013.01); *A61B 2018/00761* (2013.01); *A61B 2018/00791* (2013.01); *A61B 2018/00875* (2013.01); *A61B 2018/00904* (2013.01); *A61B 2034/104* (2016.02); *A61B 2034/105* (2016.02); *A61B 2034/107* (2016.02); *A61B 2034/2046* (2016.02); *A61B 2034/2053* (2016.02); *A61B 2090/065* (2016.02); *A61B 2090/365* (2016.02); *A61B 2090/374* (2016.02); *A61B 2090/3762* (2016.02); *A61B 2090/3983* (2016.02); *A61M 2025/0166* (2013.01)

(56) References Cited

U.S. PATENT DOCUMENTS

| | | |
|---|---|---|
| 5,662,108 A | 9/1997 | Budd et al. |
| 5,697,377 A | 12/1997 | Wittkampf |
| 5,724,978 A | 3/1998 | Tenhoff |
| 5,983,126 A | 11/1999 | Wittkampf |
| 6,019,725 A | 2/2000 | Vesely et al. |
| 6,038,468 A | 3/2000 | Rex |
| 6,240,307 B1 | 5/2001 | Beatty et al. |
| 6,317,621 B1 | 11/2001 | Graumann et al. |
| 6,322,558 B1 | 11/2001 | Taylor et al. |
| 6,515,657 B1 | 2/2003 | Zanelli |
| 6,640,119 B1 | 10/2003 | Budd et al. |
| 6,728,562 B1 | 4/2004 | Budd et al. |
| 6,826,420 B1 | 11/2004 | Beatty et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,187,973 B2 | 3/2007 | Hauck |
| 7,189,208 B1 | 3/2007 | Beatty et al. |
| 7,778,689 B2 * | 8/2010 | Boese ............... A61B 5/053 600/424 |
| 7,996,060 B2 | 8/2011 | Trofimov et al. |
| 2002/0068931 A1 | 6/2002 | Wong et al. |
| 2003/0074011 A1 | 4/2003 | Gilboa et al. |
| 2003/0220636 A1 | 11/2003 | Bowman et al. |
| 2004/0039278 A1 | 2/2004 | Wacker et al. |
| 2004/0044279 A1 | 3/2004 | Lewin et al. |
| 2004/0097805 A1 | 5/2004 | Verard et al. |
| 2004/0176804 A1 | 9/2004 | Palti |
| 2005/0015006 A1 | 1/2005 | Mitschke et al. |
| 2005/0033164 A1 | 2/2005 | Yatsuo et al. |
| 2005/0054913 A1 | 3/2005 | Duerk et al. |
| 2005/0054918 A1 | 3/2005 | Sra |
| 2005/0245814 A1 | 11/2005 | Anderson et al. |
| 2006/0017749 A1 * | 1/2006 | McIntyre .......... A61N 1/36082 345/664 |
| 2007/0043296 A1 | 2/2007 | Schwartz |
| 2007/0167706 A1 | 7/2007 | Boese et al. |
| 2007/0167726 A1 | 7/2007 | Unal et al. |
| 2008/0114235 A1 | 5/2008 | Unal et al. |
| 2008/0118135 A1 | 5/2008 | Averbuch et al. |
| 2008/0125775 A1 | 5/2008 | Morris |
| 2008/0177175 A1 | 7/2008 | Mottola et al. |
| 2008/0183070 A1 | 7/2008 | Unal et al. |
| 2008/0208031 A1 | 8/2008 | Kurpad et al. |
| 2008/0221425 A1 | 9/2008 | Olson et al. |
| 2008/0275440 A1 | 11/2008 | Kratoska et al. |
| 2008/0275465 A1 | 11/2008 | Paul et al. |
| 2009/0015818 A1 | 1/2009 | Ikeda et al. |
| 2009/0148012 A1 | 6/2009 | Altmann et al. |
| 2009/0275828 A1 | 11/2009 | Shachar et al. |
| 2009/0281566 A1 | 11/2009 | Edwards et al. |
| 2010/0063400 A1 | 3/2010 | Hall et al. |
| 2010/0217116 A1 | 8/2010 | Eck et al. |
| 2010/0249579 A1 | 9/2010 | Starks |
| 2010/0274239 A1 | 10/2010 | Paul et al. |
| 2010/0283484 A1 | 11/2010 | Cohen et al. |
| 2010/0312094 A1 | 12/2010 | Guttman et al. |
| 2011/0106221 A1 | 5/2011 | Neal, II et al. |
| 2011/0230758 A1 | 9/2011 | Eichler |
| 2012/0059249 A1 | 3/2012 | Verard et al. |
| 2012/0109115 A1 | 5/2012 | Condie et al. |
| 2012/0123250 A1 | 5/2012 | Pang et al. |
| 2012/0172724 A1 | 7/2012 | Hill et al. |
| 2012/0173217 A1 | 7/2012 | Heimbecher |
| 2012/0197243 A1 | 8/2012 | Sherman et al. |
| 2012/0238866 A1 | 9/2012 | Wang et al. |
| 2013/0137980 A1 | 5/2013 | Waters et al. |
| 2013/0272593 A1 | 10/2013 | Lee et al. |
| 2014/0088943 A1 | 3/2014 | Trayanova et al. |
| 2014/0187949 A1 | 7/2014 | Zhao et al. |
| 2014/0330111 A1 | 11/2014 | Lichtenstein et al. |
| 2016/0055304 A1 * | 2/2016 | Russell ............. A61N 1/36031 705/3 |

FOREIGN PATENT DOCUMENTS

| | | |
|---|---|---|
| EP | 2777584 | 9/2014 |
| HR | P20131208 | 3/2014 |
| JP | 2001-340336 | 12/2001 |
| WO | WO 98/01069 | 1/1998 |
| WO | WO 2007/067628 | 6/2007 |
| WO | WO 2010/102794 | 9/2010 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |

OTHER PUBLICATIONS

Communication Relating to the Results of the Partial International Search dated Aug. 22, 2016 From the International Searching Authority Re. Application No. PCT/IB2016/052688.

(56) References Cited

OTHER PUBLICATIONS

Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Search Report and the Written Opinion dated Jan. 3, 2017 From the International Searching Authority Re. Application No. PCT/IB2016/052688. (14 Pages).
International Search Report and the Written Opinion dated Oct. 12, 2016 From the International Searching Authority Re. Application No. PCT/IB2016/052686.
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Aug. 25, 2016 From the International Searching Authority Re. Application No. PCT/IB2016/052690.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Chierchia et al. "An Initial Clinical Experience With a Novel Microwave Radiometry Sensing Technology Used in Irrigated RF Ablation for Flutter", Academic Hospital Brussels, Belgium, 1 P. Jan. 1, 2011.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the UNCOVER-AF Trial," EP Lab Digest, 17(5), May 2017, 5 pages.

Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomics in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
St. Jude Medical "Cardiac Mapping System / ECG. NSite™ NavX™", St. Jude Medical, Products Sheet, 22 P., 2017.
Vandekerckhove et al. "Flutter Ablation With an irrigated Catheter Using Microwave Radiometry Sensing Technology: First Report in Men", Sint Jan Hospital, Department of Cardiology, Bruges, Belgium, 1 P., Jan. 1, 2011.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
International Preliminary Report on Patentability dated Nov. 23, 2017 From the International Bureau of WIPO Re. Application No. PCT/IB2016/052686. (11 Pages).
International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Search Report and the Written Opinion dated Oct. 21, 2016 From the International Searching Authority Re. Application No. PCT/IB2016/052687. (16 Pages).

* cited by examiner

FIDUCIAL MARKING FOR IMAGE-ELECTROMAGNETIC FIELD REGISTRATION

RELATED APPLICATIONS

This application is National Phase of PCT Patent Application No. PCT/IB2016/052692 having International filing date of May 11, 2016, which claims the benefit of priority under 35 USC § 119(e) of U.S. Provisional Patent Application Nos. 62/160,080 filed May 12, 2015; 62/291,065 filed Feb. 4, 2016; and 62/304,455 filed Mar. 7, 2016. The contents of the above applications are all incorporated by reference as if fully set forth herein in their entirety.

PCT Patent Application No. PCT/IB2016/052692 is also related to PCT Patent Application Nos. PCT/IB2016/052687 titled "SYSTEMS AND METHODS FOR TRACKING AN INTRABODY CATHETER", PCT/IB2016/052690 titled "LESION ASSESSMENT BY DIELECTRIC PROPERTY ANALYSIS", PCT/IB2016/052686 titled "CONTACT QUALITY ASSESSMENT BY DIELECTRIC PROPERTY ANALYSIS" and PCT/IB2016/052688 titled "CALCULATION OF AN ABLATION PLAN", all having the International filing date of May 11, 2016.

FIELD AND BACKGROUND OF THE INVENTION

The present invention, in some embodiments thereof, relates to the field of intra-body navigation by and sensing of electrical fields, and more particularly, to the formation of the sensed electrical fields.

Systems and methods have been developed for non-fluoroscopic tracking of intra-body catheters, for example, for tracking a catheter during a cardiac procedure, such as intra-cardiac ablation.

Frederik H. M. Wittkampf, in U.S. Pat. No. 5,983,126 describes "A system and method are provided for catheter location mapping, and related procedures. Three substantially orthogonal alternating signals are applied through the patient, directed substantially toward the area of interest to be mapped, such as patient's heart. The currents are preferably constant current pulses, of a frequency and magnitude to avoid disruption with ECG recordings. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonal applied current signals. Three processing channels are used to separate out the three components as x, y and z signals, from which calculations are made for determination of the three-dimensional location of the catheter tip within the body."

One form of catheter ablation known as RF ablation relies on heating caused by the interaction between a high-frequency alternating current (e.g., 350-500 kHz) introduced to a treatment region, and dielectric properties of material (e.g., tissue) in the treatment region. One variable affecting the heating is the frequency-dependent relative permittivity κ of the tissue being treated. The (unitless) relative permittivity of a material (herein, κ or dielectric constant) is a measure of how the material acts to reduce an electrical field imposed across it (storing and/or dissipating its energy). Relative permittivity is commonly expressed as $$\kappa = \zeta_r(\omega) = \frac{\varepsilon(\omega)}{\varepsilon_0}, \text{ where } \omega = 2\pi f,$$

and f is the frequency (of an imposed voltage). In general, $\varepsilon_r(\omega)$ is complex valued; that is: $\varepsilon_r(\omega)=\varepsilon'_r(\omega)+i\varepsilon''_r(\omega)$.

The real part $\varepsilon'_r(\omega)$ is a measure of energy stored in the material (at a given electrical field frequency and voltage), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity σ as $$\varepsilon''_r(\omega) = \varepsilon''_{rd} + \frac{\sigma}{\omega \cdot \varepsilon_0}.$$

Any one of the above parameters: namely κ, ε, $\varepsilon'_r$, $\varepsilon''_r$, σ, and/or $\varepsilon''_{rd}$, may be referred to herein as a dielectric parameter. The term dielectric parameter encompasses also parameters that are directly derivable from the above-mentioned parameters, for example, loss tangent, expressed as $$\tan\sigma = \frac{\varepsilon''_r}{\varepsilon'_r},$$

complex refractive index, expressed as $n=\sqrt{\varepsilon_r}$, and impedance, expressed as $$Z(\omega) = \sqrt{\frac{i\omega}{\sigma + i\omega\varepsilon_r}} \text{ (with } i = \sqrt{-1} \text{)}.$$

Herein, a value of a dielectric parameter of a material may be referred to as a dielectric property of the material. For example, having a relative permittivity of about 100000 is a dielectric property of a 0.01M KCl solution in water at a frequency of 1 kHz, at about room temperature (20°, for example). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: *Compilation of the Dielectric Properties of Body Tissues at RF and Microwave Frequencies* (web pages presently maintained at //niremf(dot)ifac(dot)cnr(dot)it/docs/DIELECTRIC/home(dot)html).

SUMMARY OF THE INVENTION

There is provided, in accordance with some exemplary embodiments, a method of generating a target body surface electrode configuration for producing an electromagnetic field within a region of interest within a living body, the method comprising: simulating, for each of a plurality of candidate body surface electrode configurations, a respective electromagnetic field, the simulating being based on an electrical impedance model of the region of interest in the living body; evaluating each of the respective electromagnetic fields according to at least one criterion of electromagnetic field structure within the region of interest; and selecting the target body surface electrode configuration from the candidate body surface electrode configurations, based on the evaluating.

According to some embodiments, the candidate body surface electrode configuration comprises respective positions of at least one pair of body surface electrodes.

According to some embodiments, the region of interest comprises a region of a heart.

According to some embodiments, the region of the heart comprises an atrium.

According to some embodiments, the at least one criterion comprises a criterion for evaluation of an electrical field gradient component passing through the region of interest along a superior/inferior Z-axis of the living body.

According to some embodiments, electromagnetic fields are simulated for the target body surface electrode configurations under conditions of supplying through the body surface electrodes at least one frequency of alternating current between about 10 kHz and 100 kHz with a non-zero amplitude of less than 1 mA.

According to some embodiments, at least one simulated electromagnetic field for a target body surface electrode configuration is simulated to extend between at least one body surface electrode and a probe electrode within the body.

According to some embodiments, electromagnetic fields are simulated extending between the at least one body surface electrode and the probe electrode within the body under conditions of supplying through the electrodes at least one frequency of alternating current between about 12.8 kHz and 1 MHz with a non-zero amplitude of less than 1 mA.

According to some embodiments, simulated electromagnetic fields produced by the target body surface electrode configuration comprise at least three frequencies in the range between about 12.8 kHz and 1 MHz.

According to some embodiments, the body surface electrode configuration includes specification of electrode surface shape and area.

According to some embodiments, the at least one criterion of electromagnetic field structure is for evaluation of the linearity of the electrical field gradient within a catheter-navigable lumen of the region of interest.

According to some embodiments, at least one criterion of electromagnetic field structure is for evaluation of the dynamic range of the electrical field gradient within a catheter-navigable lumen of the region of interest.

According to some embodiments, the evaluating comprises evaluating the electrical field gradient at a frequency used with an associated electrode in intra-body electrical field-guided catheter navigation.

According to some embodiments, the evaluating comprises evaluating the electrical field gradient at a frequency used with an associated electrode in intra-body electrical field-guided assessment of a lesion dielectric property.

According to some embodiments, the simulating comprises evaluating electromagnetic field equations for elements within the impedance model.

According to some embodiments, the impedance model comprises segmented anatomical data, to which tissue-type dependent dielectric properties are assigned.

According to some embodiments, the anatomical data comprise 3-D images taken by at least one imaging method of the group consisting of magnetic resonance imaging and computed tomography imaging.

There is provided, in accordance with some exemplary embodiments, a method of instructing the positioning of body surface electrodes on a living body carrying to fiducial marks, the method comprising: receiving a target configuration of comprising positions of body surface electrodes, the target body surface electrode configuration being defined in respect of an anatomical model of the living body; defining positions of the target body surface electrode configuration in respect of the fiducial marks carried on the living body; and providing instructions for positioning body surface electrodes on the living body according to the target body surface electrode configuration, wherein the instructions use the fiducial marks as references for the body surface electrode positions.

According to some embodiments, the method comprises placing the fiducial marks before acquisition of anatomical data on which the anatomical model is based.

According to some embodiments, the fiducial marks remain in place for at least one day elapsing after the acquisition of anatomical data, and until the placement of the electrodes.

According to some embodiments, the anatomical data comprise 3-D images taken by at least one imaging method of the group consisting of magnetic resonance imaging and computed tomography imaging.

According to some embodiments, the providing comprises displaying an electrode position on a photographic image of a surface of the living body.

According to some embodiments, the electrode position and the photographic image are updated on a real-time display.

According to some embodiments, displayed electrode position is determined relative to the position of one or more of the fiducial marks within the photographic image.

There is provided, in accordance with some exemplary embodiments, a method of adjusting a simulated electromagnetic field simulated to be excitable within a living body by a target configuration of body surface electrodes, the adjusting being for improving consistency of the simulated electromagnetic field with an excited electromagnetic field, the method comprising: positioning surface electrodes in an actual configuration on the living body, based on the target configuration; determining at least one difference between the actual configuration of the surface electrodes and the target configuration; and adjusting the simulation, based on the difference, to approximate the simulated electromagnetic field to an electromagnetic field excited by the actual configuration of the surface electrodes.

According to some embodiments, the adjusting the simulation comprises interpolation between a plurality of electrical field simulations for electrode positions at mutually different positions also different with respect to an electrode position in the actual body surface electrode configuration.

According to some embodiments, the different positions are within 1 cm or less of each other.

According to some embodiments, the adjusting comprises recalculation of the electromagnetic field simulation based on evaluating electromagnetic field equations for elements within an impedance model.

According to some embodiments, the determining comprises comparing the position of an electrode within a photograph of the actual configuration to a corresponding position specified by the target configuration.

According to some embodiments, the comparing comprises comparing of positions described with reference to one or more fiducial marks previously placed on the surface of the living body.

According to some embodiments, the adjusting comprises adjusting the simulation of the electrical field within a region of the heart.

According to some embodiments, the region of the heart comprises an atrium.

There is provided, in accordance with some exemplary embodiments, a system for instructing the positioning of electrodes on a living body, the system comprising at least one processor configured to: receive an anatomical model of a portion of the living body, the anatomical model comprising positions of anatomical landmarks; determine, based on the anatomical model, positions for body surface electrodes relative to the positions of the anatomical landmarks; receive a photographic image of a portion of the living body, the photographic image showing the anatomical landmarks; generate an image showing the positions determined for the body surface electrodes on the portion of the living body; and provide the image so generated to an image display.

According to some embodiments, the camera and display are integrated in a single housing.

There is provided, in accordance with some exemplary embodiments, a system for generating a target body surface electrode configuration for producing an electromagnetic field within a region of interest within a living body, the system comprising a digital computer configured to: simulate, for each of a plurality of candidate body surface electrode configurations, a respective electromagnetic field, the simulating being based on an electrical impedance model of the region of interest in the living body; evaluate each of the respective electromagnetic fields according to at least one criterion of electromagnetic field structure within the region of interest; select the target body surface electrode configuration from the candidate body surface electrode configurations, based on the evaluating; and provide the selected configuration with electrode positions specified relative to the surface of the living body.

According to some embodiments, the region of interest comprises a region of a heart.

According to some embodiments, the at least one criterion comprises a criterion for evaluation of an electrical field gradient vector component passing through the region of interest along a superior/inferior Z-axis of the living body.

According to some embodiments, the body surface electrode configuration includes specification of at least one of the group consisting of electrode position, electrode surface shape, and electrode surface area.

According to some embodiments, the at least one criterion of electromagnetic field structure is for evaluation of the linearity of the electrical field gradient within the region of interest.

According to some embodiments, at least one criterion of electromagnetic field structure is for evaluation of the dynamic range of the electrical field gradient within the region of interest.

There is provided, in accordance with some exemplary embodiments, a method of selecting a target body surface electrode configuration for producing an electromagnetic field within a region of interest within a living body, the method comprising: matching a body morphology of a patient to a body morphology type in a database comprising body morphology types associated to body surface electrode configurations; and selecting the target body surface electrode configuration to be a body surface electrode configuration from the database associated with the matched body morphology type.

According to some embodiments, the body surface electrode configuration from the database is associated with the body morphology type based on simulation in an electrical impedance model of the region of interest in the living body, and selected according to at least one criterion of electromagnetic field structure within the region of interest.

According to some embodiments, the matching and selecting are performed on a computer server at a location remote from the patient.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 3B, left atrium), according to some embodiments;

DESCRIPTION OF SPECIFIC EMBODIMENTS OF THE INVENTION

Figure 1A:
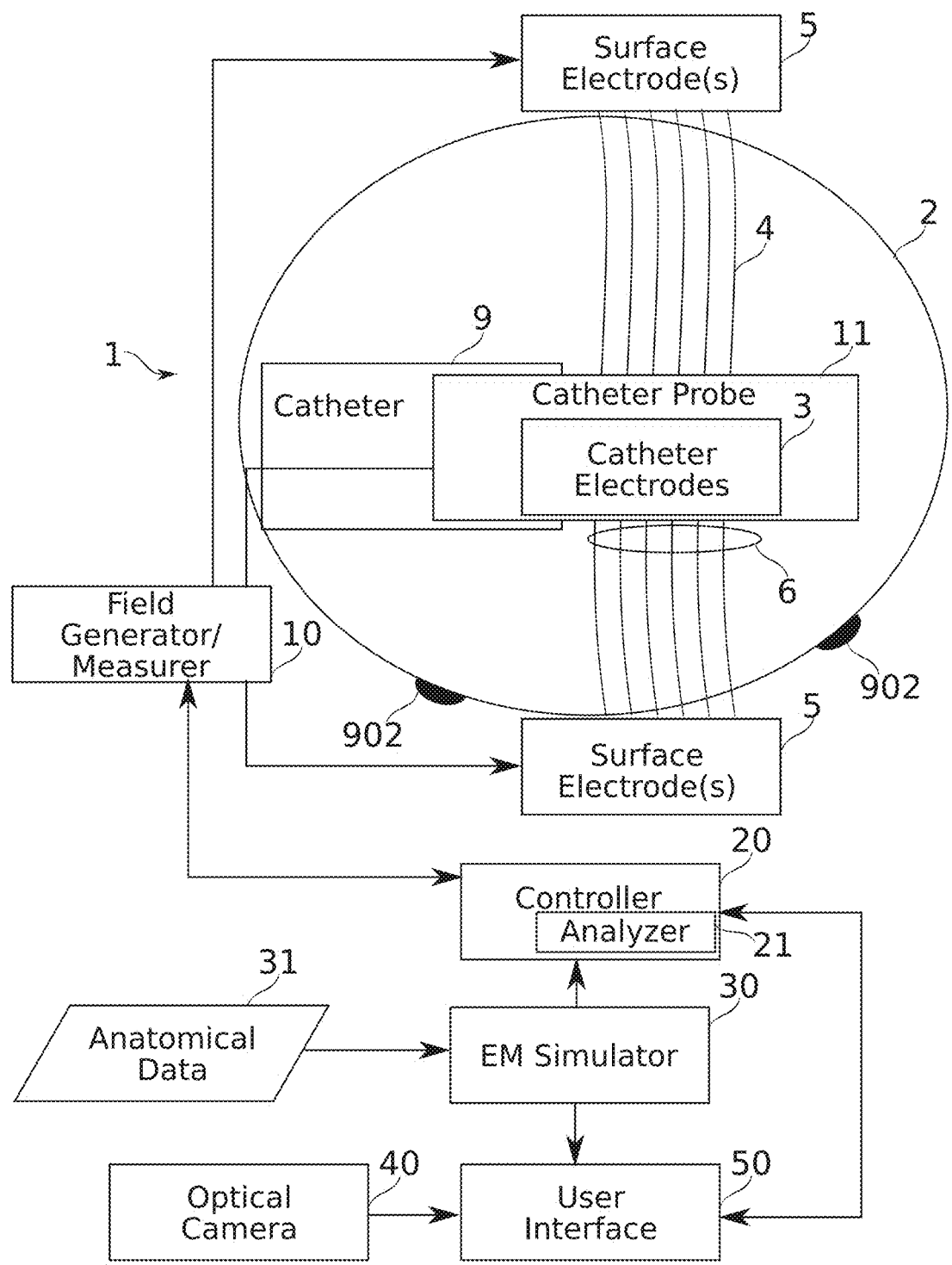
FIG. 1A schematically illustrates a system for production and intra-body sensing of electrical fields, according to some exemplary embodiments of the invention.

The present invention, in some embodiments thereof, relates to the field of intra-body navigation by and sensing of electrical fields, and more particularly, to the formation of the sensed electrical fields.

Overview

A broad aspect of some embodiments relates to the generation of electrical fields used in navigation (e.g., impedance-based navigation) and/or dielectric property-based tissue assessment within a living body.

In some embodiments, electrodes are placed on a living body to produce fields within the body for navigation of a catheter within it (the living body being, for example, of a human patient). Such navigation is used, for example, to guide a catheter probe to a particular location, such as a region of a human heart.

Optionally, the guided catheter probe includes an electrical field sensor to facilitate the navigation. To allow a user to obtain information on the location of the probe and to guide the probe to the target, a coordinate system is optionally provided by defining X, Y, and/or Z navigation axes. Optionally, a navigation axis is defined by an electrical field established between a pair of electrodes applied externally to the living body. Optionally, the origin of each axis is set to the positions where there is a 0 Volt potential difference with one of the body surface electrodes. The electrodes are optionally applied as body surface electrodes (e.g., body surface electrodes covering about 10×15 cm, or a larger or smaller body surface electrode area).

During navigation, in some embodiments, an intra-body probe senses characteristics of the electrical fields that define the different navigation axes to provide information about the location of the intra-body probe. This information may be used in the navigation of the probe to a target location. Navigation relies on distinguishing electric potential differences of only a few millivolts per centimeter, and on having good knowledge of which position corresponds to which sensed voltage or voltages.

In some embodiments, measurements of electrical fields defining different navigation axes are distinguished according to the frequency of fields generated between different body surface electrode pairs. For example, there are optionally provided between three such pairs three corresponding fields X, Y, Z which cross each other within a region of navigational interest. The fields are generated at different frequencies $f_X$, $f_Y$, $f_Z$. In the region of navigational interest, the time-varying voltage sensed by an electrode at each of these frequencies corresponds to an isopotential surface. Insofar as the locations of the three resulting isopotential surfaces are known in space, the electrode can be located to the spatial position where they intersect. Optionally, the relative locations of a plurality of electrodes on the same probe are used to establish an orientation of the probe.

According to some embodiments, features of an electrical field used for navigation optionally include:

- steep gradient—a sufficiently high voltage gradient to allow voltage difference measurements to clearly distinguish positions and/or motion within the field (while remaining safe);
- predictable gradient—sufficient spatial uniformity (for example, linearity of voltage gradient) to allow the sensed field characteristics to be readily translated into electrode position within the field.

The shape (e.g., the courses of isopotential lines which define voltage gradients) of the electrical field is influenced by the patient's tissue in which the field is excited; and by defined parameters of the field, for example, frequency, intensity, location, shape, and size of the surface electrodes, etc. The body itself is irregular in surface shape, and the surface shape moreover places constraints on the shape and positioning of surface electrodes. Electrical fields set up in different patients potentially differ from one another, according, for example, to size, weight, age, and/or gender of the patient. Furthermore, dielectric properties of body tissues within which the field is established, e.g., lung, bone, and muscle, may differ. These dielectric properties and their distribution in turn also affect voltage gradients.

In some embodiments, body surface electrodes are used in the generation of fields used for intra-body electrical field sensing applications other than navigation (e.g., tissue assessment). For example, a body surface electrode is used for generation of a field used in the assessment of tissue dielectric properties, which properties in turn potentially correlate with characteristics such as scarring, lesion state, contact force and/or quality, and/or temperature.

An aspect of some embodiments relates to the selection of body surface electrode parameters for the creation of electrical fields optimized for one or more parameters affecting electrode sensing of those fields. Electrode sensing is used, for example, in navigation-guidance and/or tissue property measurement (e.g., for tissue assessment).

In some embodiments, a target body surface electrode configuration comprises definition of one or more of the following: electrode placement on the body surface (e.g., position and/or orientation), electrode size and/or shape, electrode electrical contact with the body surface (e.g., impedance at the electrode/body surface interface, optionally including specification of an electrolyte gel, gel layer, or other surface treatment), electrode materials, and/or electrode number.

In some embodiments, electrode configurations are specified pairwise; for example, one pair per function such as to produce an electromagnetic field used as an axis of navigation and/or for sensing functions such as dielectric property sensing. In some embodiments, an electrode configuration comprises at least three pairs of electrodes; e.g., electrodes arranged to define electromagnetic fields defining three navigation axes. In some embodiments, an electrode configuration comprises at least four pairs of electrodes, of which one is optionally an electrode pair defined for measurement of tissue properties such as tissue dielectric properties.

In some embodiments of the invention, fields produced by a particular body surface electrode configuration are simulated using a model of dielectric properties of the medium residing between the electrodes. This medium may include tissues of variable types, and tissue of each type may have its own dielectric characteristics. A dielectric characteristic is any characteristic quantifiable by a parameter relating to the relative permittivity of the medium; for example, by the real part thereof, the imaginary part thereof, the ratio between real and imaginary parts, etc. Optionally, modeling is performed de novo for an individual, and/or approximated based on a reference model. Optionally, CT and/or other anatomical data are used to create a model of tissue type locations within a body, to which dielectric properties are assigned. Optionally, tissue types in the model are assigned dielectric properties; for example, according to known and/or estimated dielectric properties of blood, air, lung, heart, bone, skin and/or other tissue and/or material types.

In some embodiments, one or more reference models are generated based on CT and/or other anatomical data. For example, a reference model comprises a composite of anatomical data from two or more individuals, and/or an interpolation between anatomical data from two or more individuals. Optionally, a reference model is adjusted to the specifics of an individual (for example, adjusted for weight, size, and/or body fat).

In some embodiments, simulated fields within the body (more particularly, within a targeted region of the body) are evaluated from models of two or more body surface electrode configurations. Optionally, evaluation comprises computerized application of the electromagnetic field equations to a dielectric property model, in combination with parameters of body surface electrode placement, size and/or operation. Optionally, evaluation takes into account temperature differences through the simulated anatomy (e.g., differences which potentially affect dielectric properties). Parameters of electrode operation may include, for example, frequency of field set up between the electrodes, potential difference between electrodes, etc.

In some embodiments, a body surface electrode configuration is selected from among the plurality of evaluated configurations for use in a procedure, based on properties of the simulated fields which the body surface electrode configuration would produce within the body. Field properties used as a basis for selection optionally include, for example, electrical potential gradient strength, and/or electrical potential gradient uniformity (for example, linearity).

In some embodiments, parameters of body surface electrode placement, size, and/or shape are selected to optimize field potential gradient linearity and/or gradient strength. Optionally, the optimization is targeted to a particular region of the body (for example, the heart). Optionally, the optimization is targeted more specifically at a portion of the particular region of the body, e.g., a portion targeted for treatment (for example, more particularly at a region near a left atrial appendage). Optionally, the optimization is targeted to one or more particular phases of respiration and/or heartbeat, for example, end expiratory end systolic, which may be phases used in 3-D image acquisition and/or reconstruction.

In some embodiments, electrical field-guided navigation of a probe is performed within the body; the navigation comprising assessment of probe position in space based on electrical field measurements. Typically, potential gradient position within respective X, Y, and Z electrical fields dominates the measurement of spatial position along a respective cardinal spatial axis. The fields as a whole are not necessarily homogenous or mutually orthogonal, but do establish field components falling along the orthogonal spatial axes. Herein, unless otherwise noted, the X and Y fields are considered to cross in the transverse plane of the body. Optionally, The X field extends across the body left and right, while the Y field extends between ventral and dorsal positions. Optionally—and particularly for sensing in the thoracic and abdominal cavities—body surface electrode positions are selected so that fields cross the body in about the cardinal directions, between electrode positions bracketing the region of interest as closely as possible. Nevertheless, the simple positioning rules just described for X and Y electrode pairs are not necessarily optimal with respect to any given internal region of interest, and potentially benefit from adjustment as described herein.

Determination of an optimal Z-field configuration is optionally subject to further considerations. For example, there are potentially several surface placement options for electrodes which can establish a field having a Z-axis component (component along the superior/inferior body axis) that extends through the heart region—but there may be none which distinguish themselves as optimal based on simple positioning rules. For example, one body surface electrode could be placed on the upper back (centered or on either shoulder), while the second could be placed on the lower ventral abdomen where a line extending between the two body surface electrodes intersects the heart (left, right, and/or center). Alternatively, lower back/upper chest regions could be selected.

Which positioning is best for a given set of optimization criteria (e.g., steepest potential gradient and/or most linear in field potential generated through the heart region) is potentially affected by details of individual patient anatomy. For example, the further apart the two Z electrodes are, the lower the field potential gradient. However, depending on body shape and/or size, more distant positioning potentially also brings the field orientation closer to the superior/inferior body axis, maximizing the magnitude of the gradient useful for navigation along that direction. It can also be understood that the electrode positioning which creates the steepest potential gradient is not necessarily the same as the positioning that creates the most linear potential gradient.

In some embodiments, external surface electrodes are positioned for use in measurement of tissue properties. For example, one or more catheter probe electrodes (for example as described in relation to FIG. 1A, herein) are introduced internally (e.g., to a heart chamber), and used in combination with one or more surface electrodes to measure dielectric properties of tissue in between them. Optionally, probe electrodes are dedicated to the creation of fields used in tissue dielectric property measurement, rather than in spatial position measurement. It is a potential advantage to position the external surface electrodes where tissues of interest for measurement are localized in a region where fluctuations affecting sensing (for example, due to respiratory or cardiac movement) and/or positioning have the lowest effect on measured result. In some embodiments, another external body surface positioning electrode parameter which is optimized is the relative impedance of electrodes used in the measurement of dielectric properties of tissues. For example, such electrodes are placed with sizes and/or electrolytic surface treatments (e.g., gels) which give them a lower relative impedance compared to other electrodes in the overall body surface electrode configuration.

In some embodiments, options for electrode position parameters for a patient are selected based on similarity between the patient's anatomy and a modeled anatomy selected from a bank of modeled anatomies (based, e.g., on a database of actual patient anatomies) for which electrical field simulations have been previously created. In some embodiments, a modeled anatomy used in producing an electrical field simulation is matched to known anatomy; for example, by scaling and/or morphing. Optionally, the simulation from the simulation bank where the simulation anatomy most closely matches (e.g. needs the least changes to match) the patient anatomy is selected as the simulation basis. In some embodiments, non-image data is used (optionally, used exclusively or together with image data) to select simulation from the simulation bank: for example, the patient is matched to an existing simulation based on parameters of weight, age, gender, physical size, and/or another parameter). Where a specific region is of interest (for example, the heart), selection is optionally weighted based on anatomy in that region in particular (for example, a degree of ventricular hypertrophy).

An aspect of some embodiments relates to use of fiducial marks located on a body as a reference for the positioning of body surface electrodes to match a simulated target configuration.

In some embodiments, fiducial marks are used to guide the body surface placement of body surface electrodes used to produce sensed electrical fields during an intra-body procedure. Optionally, once placed, the fiducial mark is persistent; for example, for at least a day, at least a week, at least 4 weeks, or for another longer, shorter, or intermediate period. Optionally, the time of persistence is long enough to span the time between initial 3-D imaging (e.g., CT or MRI imaging) producing data used in electromagnetic simulation for catheter procedure pre-planning, and the catheter procedure itself. Persistent fiducial marks provide the potential advantage of unambiguously allowing alignment between an electromagnetic simulation and 3-D image data to be accurately transferred back to electrode positions on the actual body of a patient.

In some embodiments, target body surface electrode positions are selected based on use of an electromagnetic simulation which is based on and/or registered relative to anatomical data (for example, 3-D image data) of a patient. Optionally, the target body surface electrode positions are specified in advance of the beginning of a catheterization procedure (pre-planned). Optionally, the anatomical data itself is registered relative to the positions of fiducial marks locatable (for example, visually or by electronic sensing) after 3-D imaging completes. Optionally, the fiducial marks are persistently placed markings. Optionally, the selected target body surface electrode locations are described (for example, by automatically produced instructions for placement provided to a technician) relative to the locations of the fiducial marks. Optionally, the description is relative to the surface of the patient body; for example in terms of distances and/or directions along a body surface.

In some embodiments, a method of aligning sensed voltages within a generated electrical potential field gradient to spatial position within a patient body comprises selecting, relative to positions defined in 3-D imaging data, the body surface electrode positions expected to produce the electrical potential field gradient; selecting, relative to positions defined in the 3-D imaging data, the positions of fiducial marks on a patient body surface; calculating positions on the patient body surface relative to the fiducial marks which correspond to the body surface electrode positions; providing descriptions of those relative positions along the patient body surface which can be measured out to find correct positioning of the body surface electrodes; and placing the body surface electrodes themselves in those positions.

In some embodiments, a placed fiducial mark comprises a temporary tattoo. The temporary tattoo comprises, for example, an ink marking, an injected marker, and/or a peel-off temporary tattoo. Optionally, the temporary tattoo comprises an electronic identification component, such as an RFID chip assembly. The placed fiducial mark is optionally of any suitable shape, but preferably has at least one focus which is readily identified (such as the intersection region of a cross-hair). Optionally, the fiducial mark also has a clearly distinguishable orientation (for example, the orientation defined by a line orientation, and/or by the relative orientation of two or more separated foci). Where a fiducial mark comprises an RFID or other electronic tag, a tag ID can be used to ensure that fiducial marks are correctly distinguished and identified. Optionally, the location of the tag itself is detected by an electronic message exchange (for example, an RFID response and/or a scanner detection is optionally triggered when the scanner is immediately over the electronic tag). Optionally, the tag ID comprises a resonance circuit configured so that the tag is distinguished by its resonant frequency.

In some embodiments, 3-D imaging fiducial marks are optionally placed at the same location as a persistent fiducial mark during 3-D imaging, and then removed. Optionally, the persistent fiducial mark is itself visualizeable during 3-D imaging. Optionally, the placed fiducial mark comprises two or more parts: a persistent part, and a non-persistent part which is removed after imaging.

An aspect of some embodiments relates to using feedback from observed body surface electrode positioning to refine an electromagnetic simulation for use in intra-body electrical field sensing applications.

In some embodiments, target parameters for sizing and placement of body surface electrodes are initially selected; for example, based on simulation of electromagnetic fields set up in the body of a patient from simulated body surface electrodes. In some embodiments, body surface electrodes are placed according to the target parameters (optionally guided by fiducial markings, for example as described herein). Assuming actual placement matches target placement, electromagnetic simulation is optionally then used in the conversion of subsequent intra-body electrical field sensing data to parameters of interest. The parameters of interest comprise, for example, position of a probe and/or characteristics of tissue near the probe.

However, actual body surface electrode positions and/or sizes used in a procedure are potentially different from those reflected in the initial intra-body electromagnetic simulation. This can occur, for example, simply because of placement uncertainty, because of placement constraints encountered during patient preparation, and/or due to judgment exercised at the time of the procedure. In this situation, adjustment of the simulation itself is optionally performed.

In some embodiments of the invention, body surface electrode positioning is verified and/or remeasured after placement, for example by optical photography. Optionally, positioning is measured with respect to persistent fiducial marks. Optionally, the actual positions are compared to the intended positions, and a determination made as to whether they are the same (or effectively the same) as planned, or not. In some embodiments of the invention, two or more optical photographs used to measure body surface electrode location are processed by a 3-D stereoscopic algorithm to locate the body surface electrodes in space, and/or to help ensure accurate measurements of distances relative to landmarks (such as fiducial marks).

In some embodiments, actual body surface electrode positioning is used in adjusting and/or recalculating a simulation of an electrical field within the body. Optionally, a sufficiently large mismatch in some position parameter for one or more of the electrodes (e.g., position difference between planned and actual body surface electrode positions which is larger than a threshold) results in a warning to the operator. Optionally, the threshold for warning is, for example, 1 mm, 2 mm, 5 mm, 10 mm or another larger, smaller, or intermediate position difference. Additionally or alternatively, the electrical field simulation for the planned body surface electrode positioning is updated according to the actual body surface electrode positions. Optionally, a warning is raised to the operator if the field characteristics of the updated electrical field simulation are too far from the targeted characteristics (for example, if the field strength and/or linearity simulated to be obtained with the actual positions is smaller than the field strength and/or linearity simulated to be obtained with the actual electrode positions by more than a predetermined factor).

In some embodiments, the updated field simulation is produced from the original field simulation by a computationally efficient method, for example a "morphing" distortion of the original simulation to match the actual characteristics, a re-calculation beginning from the known simulation result (rather than de novo), or another method of partial recalculation based on relatively low computational cost transformation rules. A potential advantage of this is to avoid computationally expensive full recalculation. Optionally, a warning is raised if the morphing requires too large a change to produce a reliable result. In some embodiments, no updating adjustment is made for differences below a threshold of, for example, about 1 mm, 2 mm, or another larger, smaller, or intermediate value. Potential causes of initial mismatch between modeled and actual field voltages include, for example, variations in electrical contact between probe and skin surface, which may be due more specifically (for example) to problems with the age or production of a gel used in electrode placement, and/or to hydrosis state of the patient (potentially affected by temperature, stress, and/or drug reactions).

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Example of a System for Intra-body Electrical Field Production and Sensing

Reference is now made to FIG. 1A, which schematically illustrates a system 1 for production and intra-body sensing of electrical fields 4, according to some exemplary embodiments of the invention.

In some embodiments, intra-body electric fields are sensed for field-guided navigation of a catheter probe 11. In some embodiments, intra-body electric fields are sensed for the detection, planning, creation, and/or assessment of tissue lesions and/or quality of contact with tissue (optionally including tissue targeted for lesioning). In some embodiments, assessed lesions are for treatment, for example, of atrial fibrillation, hypertrophic obstructive cardiomyopathy, euro modulation, and/or tumors.

In some embodiments, system 1 comprises an electrical field generator and measurement device 10, connected to drive current to and/or sense potentials experienced by one or more catheter electrodes 3, and a set of body surface electrodes 5 to generate at least one time-varying electrical field 4 therebetween. In some embodiments, a catheter probe 11 comprising the catheter electrodes 3 is introduced to the region of a tissue to be ablated by means of a catheter 9. In some embodiments, the body surface electrodes 5 are externally applied, for example, to the body of a patient. As a result, field 4 is induced in tissue 2 (for example, tissue of a patient's body) separating two or more body surface electrodes 5, and/or the catheter electrodes 3 and the body surface electrodes 5.

Optionally, the region through which the field 4 extends also includes a target tissue region 6. Target region 6 is optionally targeted for one or both of lesion assessment and/or ablation (lesion formation). Measurements of impedance between pairs of electrodes 3, 5 reflect electrical properties of tissue in the field region between them (in particular, dielectric properties). The dielectric properties of the tissue in turn are affected, for example, when tissue undergoes lesioning, and/or as a function of a quality of contact (which may correlate, for example, with contact force) between an electrode and the tissue.

Optionally, the number of catheter electrodes is, for example 2, 3, or 4 electrodes. Optionally, the number of body surface electrodes is, for example, 4, 6, or 8 electrodes. Optionally, electrodes are configured through connecting circuitry to allow electrical interconnection in combinations defining a plurality of electrode pairs. In some embodiments, at least some body surface electrode pairs are arranged to generate a one or more electrical fields defining a spatial axis for navigation of the catheter. Optionally or additionally, one or more electrodes are used in sensing of tissue properties for tissue assessment. More particularly, in some embodiments, one or more electrodes are used in a pairing with an intra-body probe electrode for sensing of tissue dielectric properties: for example, relative permittivity (optionally, apparent relative permittivity within the context of the circuit set up by the electrodes and field generator), dielectric conductivity, phase and/or loss components associated with the complex values (imaginary/real) of a measure of permittivity, dielectric dispersion, dielectric relaxation, or another measure which comprises a measure of one or both components of the complex-valued, frequency-dependent relative permittivity of the tissue.

Optionally, the characteristics of the time-varying electrical field are chosen to be appropriate to a measurement function which is to be performed. Typically (for measurement functions), the frequencies of the electrical field used are in the range of 40 kHz to 2 MHz. In some embodiments, use of multiple frequencies allows sampling of frequency-dependent impedance properties throughout a frequency range. Optionally, the number of frequencies used is, for example, 10 or fewer frequencies. Optionally, the number of frequencies used is, for example, 5 or fewer, 15 or fewer, 20 or fewer, or 30 or fewer.

Optionally, the frequencies are distributed evenly throughout the full range of frequencies chosen. Optionally, frequencies chosen are concentrated in some particular range. For example, for lesion assessment, frequencies in the upper portion of this range are optionally used (for example, frequencies in the range of 1 MHz to 2 MHz). Applied voltages are preferably in the safe range for use in humans, for example, 50-500 millivolts. In particular, a typical maximum safe current is about 1 milliamp, with a typical circuit resistance of about 100Ω. Resulting field strengths are in the range, for example of a several millivolts per centimeter; for example, 10 mV/cm, 20 mV/cm, 30 mV/cm, or another larger, smaller, or intermediate value. In some embodiments, the field gradient required to achieve reliable navigation is determined by the ability to distinguish between at least two electrodes (e.g., the two electrodes positioned furthest from one another) on a navigating catheter probe. In some embodiments, for example, distinct voltages measured between at least two such electrodes are used to determine of an orientation of the electrode-carrying probe. In some embodiments, a minimum voltage distinguishable between the two most mutually distant electrodes on an electrode-carrying probe (for some suitable assumption of signal-to-noise conditions) defines a lower bound for an acceptable field strength.

In some embodiments, configuration of body surface electrodes 5 (size and position, for example) is according to parameters which are selected as part of procedure planning. Optionally, electromagnetic simulation (EM simulation) is used at least in part for selection of these parameters. Optionally, the same or a related EM simulation is also used during a catheterized procedure, for example in order to guide the catheter probe 11. In some embodiments, an EM simulator module 30 is provided as part of the system. Optionally, the EM simulator 30 is configured to perform simulation based on anatomical data obtained from the patient (3-D CT or MRI image data, for example). Exemplary commercially available simulation tools that may be used as a framework for generating simulations described herein include: Sim4Life (available from Zurich Med Tech), COMSOL Multiphysics®, and CST Design Studio™.

In some embodiments, a method of correlation is optionally used to relate measured electrical properties (dielectric-related properties in particular) of tissue to lesion results. It can be understood that any sufficiently dense sampling of frequencies may be initially measured with respect to a particular system and set of tissue conditions as a basis for selecting which frequencies show the most useful results. The reduction to a number practical for field use can be based on which frequencies yield data having the greatest statistical correlation with results. It has been found by the inventors that ten or fewer frequencies, from range of 40 kHz to 2 MHz are useful to allow tissue state assessment (for example, lesion size assessment). In some embodiments, the frequencies used include at least three frequencies in a range from about 12.8 kHz to about 1 MHz. Frequencies of about 10-100 kHz are typically used in electrical field-based intra-body navigation applications. It should be noted that published permittivity and conductivity values of many tissues, including heart, are roughly linear in log:log plots over ranges of a few hundred kHz within the range mentioned, which potentially allows distinctions among tissue types to be made without a requirement for dense frequency sampling.

In some embodiments, catheter probe 11 is optionally used for ablation by RF ablation energies delivered (for example, at about 500 kHz) through the catheter electrodes 3; optionally these electrodes are also used for measurements. In some embodiments, other electrodes, another catheter probe and/or another ablation method is used, for example, cryoablation, ultrasound ablation, laser ablation, electroporating ablation, or another form of ablation. Catheter probe 11 optionally comprises at least one catheter electrode 3 which is used in sensing electrical field 4 for navigation. Optionally, an electrode 3 is configured for use in any one or more of the functions of navigation, ablation, and tissue measurement. Optionally, one or more of these functions is separately isolated to one or more designated electrodes.

In some embodiments, the electrical field generation and measurement device 1 is under the control of controller 20, which itself is optionally under user control through user interface 50. Controller 20 optionally comprises a computer with CPU or other digital hardware operating according to programmed code. Controller 20 is described herein as a multi-functional module; however, it is to be understood that functions of controller 20 are optionally distributed among two or more modules of the system.

Electrical field generation by device 1, for example, to establish navigation fields and/or probe dielectric properties of tissue by means of impedance measurements, is under the control of controller 20. Optionally, measurements from device 1, for example, those for use in measuring dielectric properties and/or field position sensed by catheter electrodes 3, are communicated back to the controller 20. In some embodiments, controller 20 is also an ablation controller. Ablation is optionally via electrical fields (e.g., RF electrical fields) generated by device 1, or by another ablation method, for example as described herein.

In some embodiments, controller 20, comprises a measurement analyzer 21 (optionally, a separate measurement analyzer is provided), relating measurements to one or more additional parameters.

In some embodiments, controller 20 comprises a measurement analyzer 21. Alternatively or optionally, measurement analyzer 21 is external to controller 20, and in some embodiments, external to system 1.

In some embodiments, measurement analyzer 21 relates received electrical measurements to one or more additional parameters. For example, EM simulator 30 optionally provides to analyzer 21 simulated electrical field data, on the basis of which sensed electrical field data is converted into position(s) of catheter electrode 3. Optionally the conversion is also based on information about the positions of body surface electrodes 5, and/or anatomical data 31 describing electrical field propagation properties of tissue 2 and/or target region 6. In some embodiments, anatomical data 31 comprise image data allowing specification of tissue types present in regions through which field 4 is induced. Optionally, anatomical data 31 comprise a dielectric property model of the anatomy, for example, dielectric properties inferred from image data and/or typical dielectric properties of different tissue types. Optionally, the model is refined by additional data received by electrode sensing, for example, sensing from catheter electrodes 3 and/or body surface electrodes 5. Electrical field simulation based on these inputs is carried out by EM simulator 30. In some embodiments, user interface 50 is provided with controls allowing selection of how controller 20 uses the other inputs to the analysis—for example, to review and/or correct alignment, adjust model parameters, and the like. The interface is also optionally used for controlling and/or displaying information from EM simulator 30.

In some embodiments, one or more optical cameras 40 are used to assist in the placement of body surface electrodes 5. Optionally, images from the optical camera 40 are used to guide placement of surface electrodes 5 against tissue 2. Optionally, the images verify placement. Optionally, images show a difference between targeted and actual placement, which can be communicated to the EM simulator to allow adaptation of the simulation results it produces. In some embodiments, fiducial marks 902 are placed on the surface of tissue 2. Optionally optical guidance of body surface electrode placement comprises imaging of fiducial marks 902 by optical camera 40. The fiducial mark 902 positions in the resulting images are used to guide where surface electrodes 5 are to be placed, and/or actually are placed.

Anatomy and Electrode Pad Modeling and Electromagnetic Field Simulation

Figure 1B:
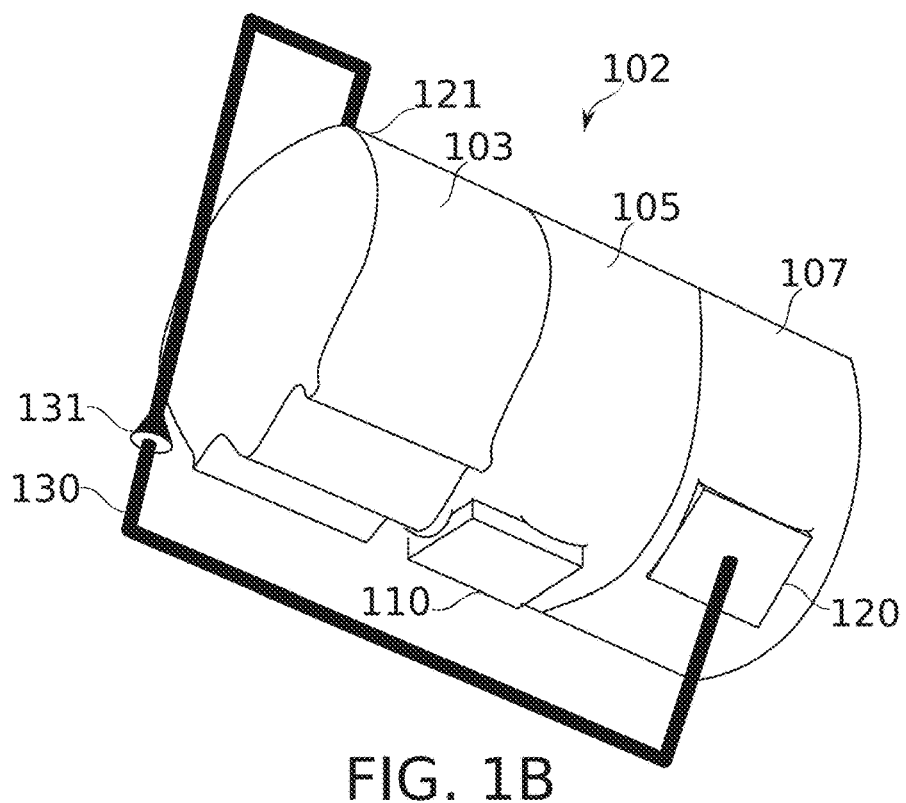
FIGS. 1B-1C schematically illustrate simulated body surface electrode positions relative to a simplified volume of tissue, according to some embodiments.
Figure 1C:
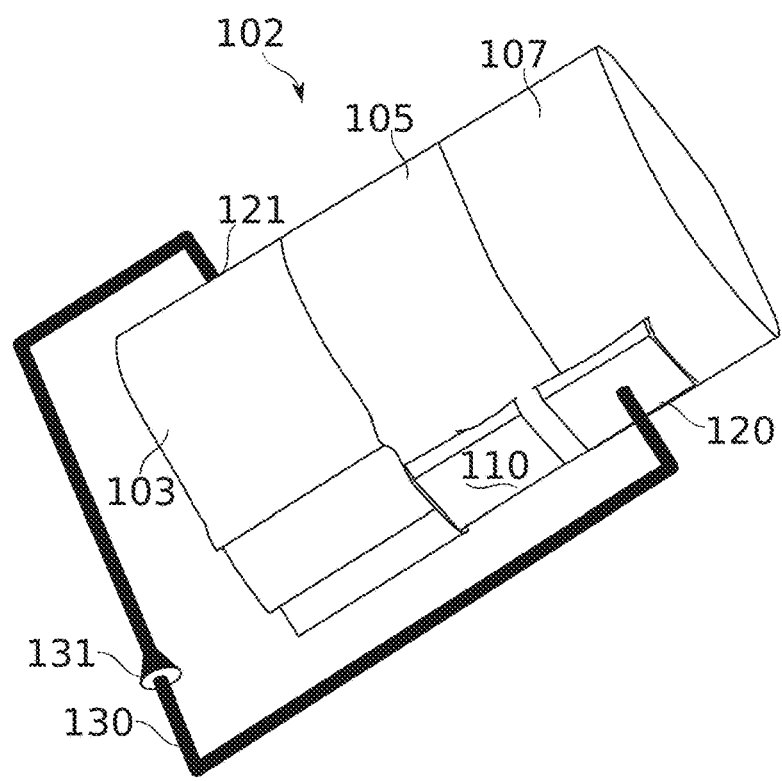

Reference is now made to FIGS. 1B-1C, which schematically illustrate simulated body surface electrode positions relative to a simplified volume of tissue 102, according to some embodiments.

FIG. 1B-1C illustrate two different positionings of the Z-field body surface electrodes 120, 121, relative to a simplified volume of tissue 102. The Z-field body surface electrodes 120, 121, establish an electrical field having a component running generally in the direction of the superior/inferior body axis, although the field overall is constrained to be somewhat diagonal to this axis due to limitations of body surface geometry. Also shown is one of the Y-field body surface electrodes 110; X-field body surface electrodes are not shown.

Tissue volume 102 comprises three sections 103, 105, 107. The middle section 105 comprises the region of navigational interest in this case (e.g., the heart). Region 103 corresponds to the upper spine and shoulders, and region 107 comprises the lower abdominal area. Examples shown are taken from a CT image-based porcine model.

In FIG. 1B, Z-field body surface electrode 120 is positioned over the left-lower abdominal region. Z-field body surface electrode 121 (hidden) is placed over the right-back shoulder. Connection 130 and signal generator 131 are schematically represented as a part of the circuit driving the electrodes at 10 kHz with a 1 V voltage amplitude.

In FIG. 1C, Z-field body surface electrode 120 is positioned over the mid-lower abdominal region. Z-field body surface electrode 121 (hidden) is placed over the spine in the nuchal region.

Figure 2A:
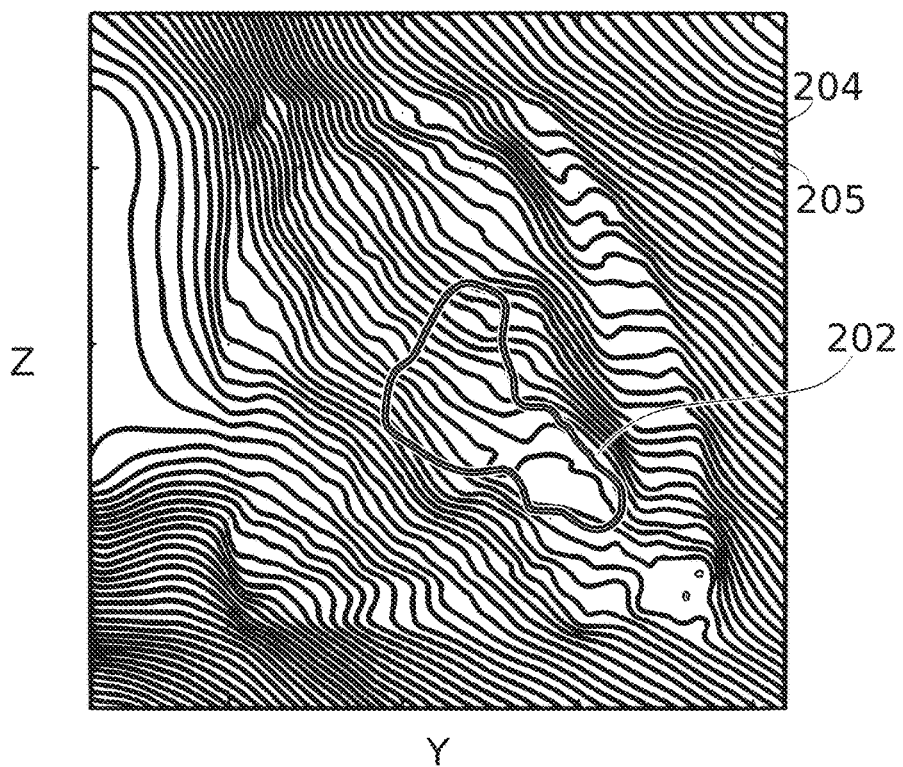
FIGS. 2A-2B show equipotential field lines for simulated conditions of different body surface electrode placement, according to some embodiments.
Figure 2B:
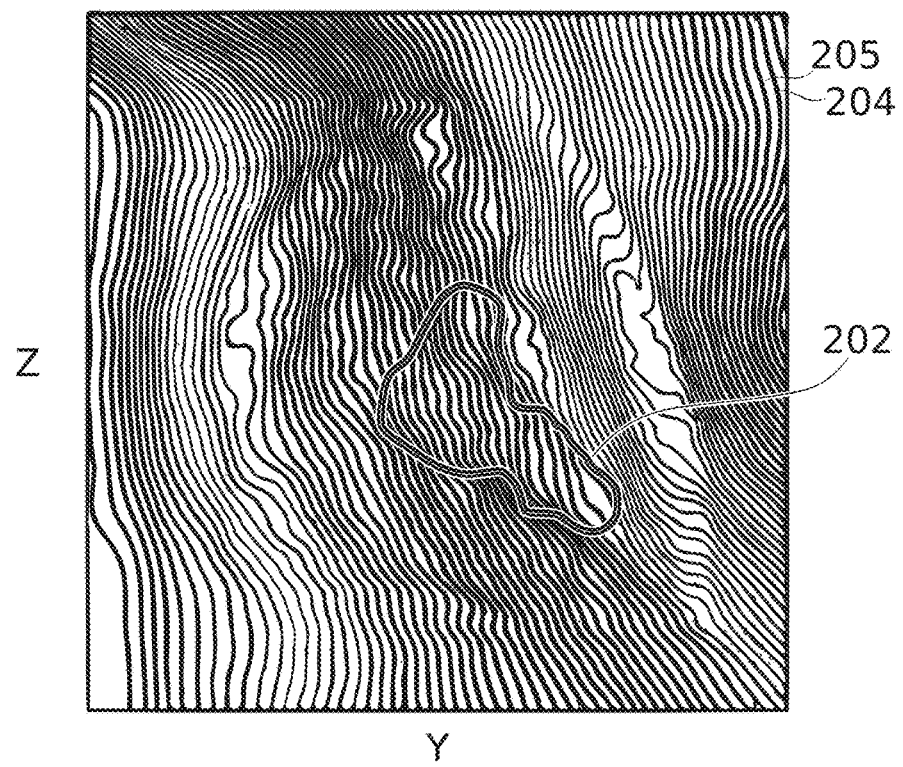
Figure 12:
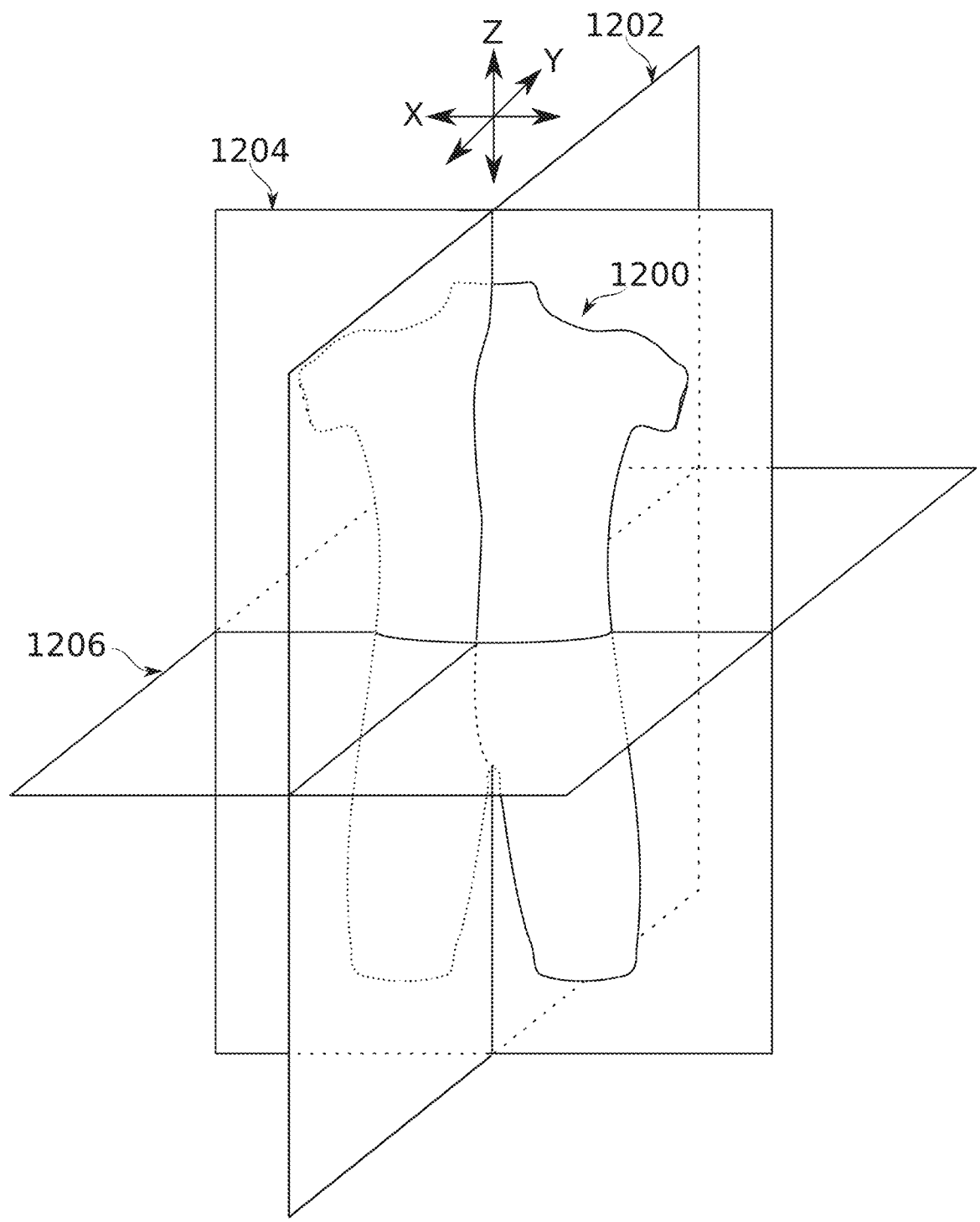
FIG. 12 illustrates a body-centered coordinate system referred to herein, according to some embodiments.

Reference is now made to FIGS. 2A-2B, which show equipotential field lines for simulated conditions of different body surface electrode placement, according to some embodiments. Reference is also made to FIG. 12, which illustrates a body-centered coordinate system referred to herein, according to some embodiments. A torso 1200 is shown for reference, crossed by three orthogonal planes: the median or sagittal plane 1202; the frontal or coronal plane 1204, and the transverse or axial plane 1206. X, Y, and Z axes shown with arrows indicate the orientations of coordinate axes referred to by the same letters with respect, for example, to electrical fields established by body surface electrode pairs.

FIGS. 2A-2B show simulated equipotential lines 204, 205 in the area of and within a Y-Z plane cross-section of the left atrium 202 (total sectional area shown is 200 mm by 200 mm). The distance between equipotential lines 204, 205 is 10 mV in each figure. In FIG. 2A, the equipotential lines within the left atrium run generally at a large angle (for example, at least 45°, 60°, 80°, or another larger, smaller, or intermediate angle) to the anatomical Z-axis, allowing their use to indicate position along this axis. In FIG. 2B, the equipotential lines run generally at a small angle to the anatomical Z-axis, making them less useful position sensing along this axis. However, they do establish a gradient which is potentially useful for sensing of anatomical Y-axis position.

The field lines shown here are simulated for a driving frequency of 10 kHz. In some embodiments, simulated driving frequency is within, for example, about 10 kHz-100 kHz. At such frequencies, wavelengths are many orders of magnitude larger than the body. This allows simplifying the simulations to be solved under the well-known quasistatic approximation (allowing, for example, relativistic propagation effects to be ignored).

Also at these frequencies, the dielectric constants of many body tissues are in the range of a few hundred to a few thousand, higher than other materials (for example, metallic leads and electrodes) in the circuit; similarly, electrical conductivity is low compared to these materials, at about 0-1 S/m. This helps to cause more of the electrical field's potential drop (and thus more of the equipotential lines) to exist within the body.

In some embodiments, simulation results are obtained by applying the well-known electromagnetic field formulae to a volume modeled to contain material having the dielectric properties associated with the tissues imaged in the CT scan (or other anatomical data). In some embodiments, tissue type identity is assigned based on automatic segmentation of the image results. It is a potential advantage to use a higher-resolution scan (for example, a CT scan with slices of between 1 mm-3 mm, or higher resolution should it be available, is preferable) as a basis of the segmentation, as this sets the conditions of the field simulation more nearly to the actual situation. In some embodiments, post-processing, optionally manually guided, is performed to remove segmentation artifacts. Optionally, post-processing, e.g., for cleaning up segmentation, uses capabilities of commercially available imaging system, such as a Carto or Insight system. In some embodiments, post-processing is performed under the guidance of an imaging technician experienced in tasks of anatomical segmentation. In general, results of the electromagnetic simulation are dependent on the degree of care devoted to obtaining accurate, high-resolution anatomical data. This resolution should also be preserved in the simulation modeling itself.

In some embodiments, simulated fields reflect a particular respiratory and/or heartbeat phase, for example, the phase associated with anatomical image acquisition and/or reconstruction. Optionally, simulations are adjusted to approximate field conditions in one or more other phases, for example, by re-spacing isopotential lines according to anatomical changes (lungs filling with air, heart chambers filling with blood) that occur during respiration and/or heartbeat.

Rules of thumb potentially observable in simulation results include: voltage dynamic range is typically increased by closer placement of body surface electrodes to the region of interest, positioning of body surface electrodes on a line crossing the region of interest, placement with the body surface electrodes facing one another across the body, and/or by use of body surface electrodes with a smooth contour (avoiding protrusions and/or sharp corners, for example). Linearity is typically enhanced when the body surface electrodes are larger, more distant from each other, and/or more distant from the region of interest. It may be understood from this that an optimal choice of placement parameters is dependent in part on the relative weighting given to linearity vs. dynamic range.

Notwithstanding these rules of thumb, both linearity and dynamic range are affected to a large extent by body habitus (physique), organ size and tissue composition. Electromagnetic simulation potentially allows selecting body surface electrode positionings which take these differences into account.

Scoring Electromagnetic Field Simulation Results

Figure 3A:
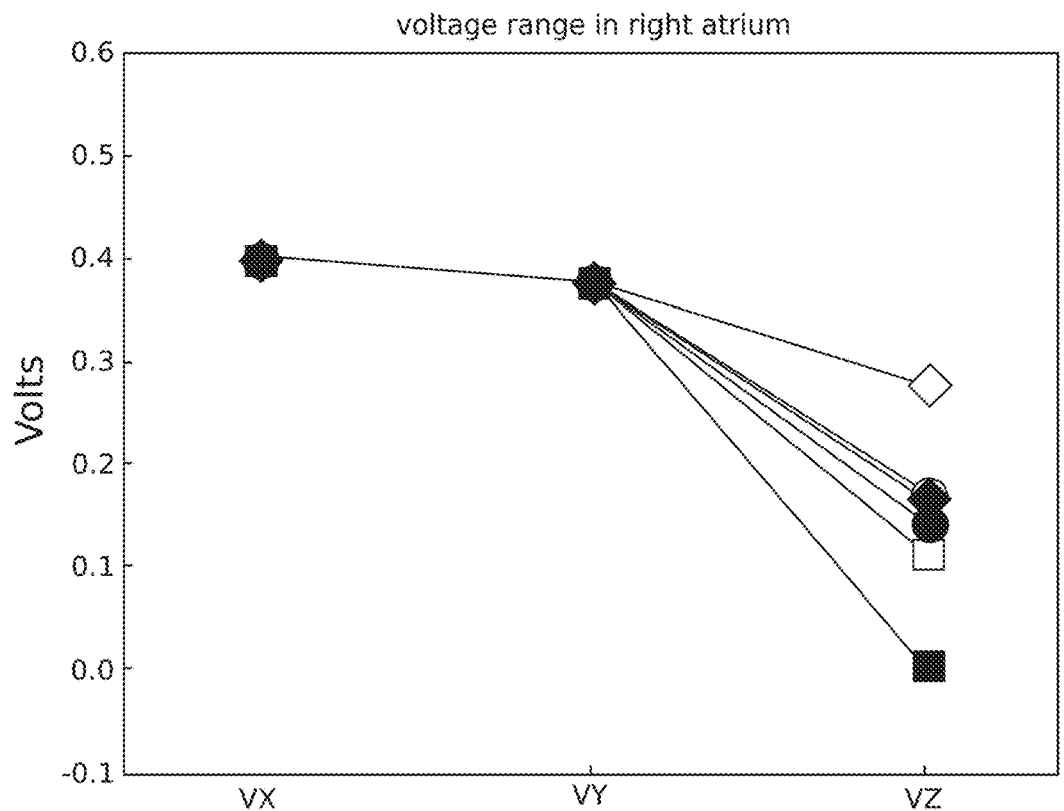
FIGS. 3A-3B show simulated voltage ranges in atrial heart chambers (FIG. 3A, right atrium.
Figure 3B:
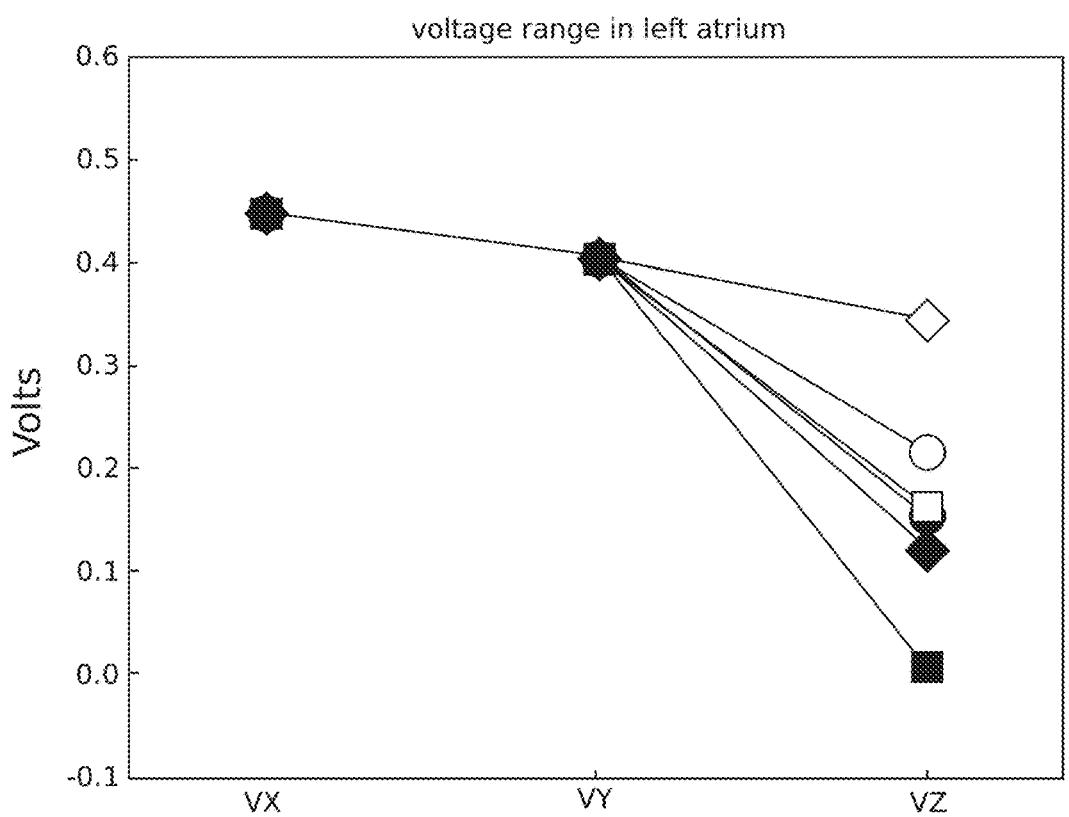

Reference is now made to FIGS. 3A-3B, which show simulated voltage ranges in atrial heart chambers (FIG. 3A, right atrium; FIG. 3B, left atrium), according to some embodiments.

In some embodiments of the invention, selection of body surface electrode positioning conditions is accomplished by comparison of simulated field results scored for one or more criteria.

FIGS. 3A-3B show examples of scores of voltage range for different body surface electrode configurations within two regions of interest: the left atrium, and the right atrium. Voltages along the X, Y, and Z axes are represented at VX, VY, and VZ, respectively. In case shown, only parameters affecting VZ are changed among the various conditions. Optionally, scoring is based on the largest and smallest potential values seen within each chamber, based on the voltage range across a particular path crossing each chamber, or by another scoring method. Of the conditions shown, one (indicated by an open diamond symbol) consistently has a higher range in both heart chambers, and so is preferable under this criterion. It is also possible for different regions to have maximal ranges for different conditions. Optionally, the choice is made by a weighting. Potentially, the condition chosen is not maximal in either region, but is sufficiently large in both. Optionally, body surface electrodes are placed to allow navigation by one body surface electrode pair in one chamber (or other region), and a different body surface electrode pair in another.

Figure 4A:
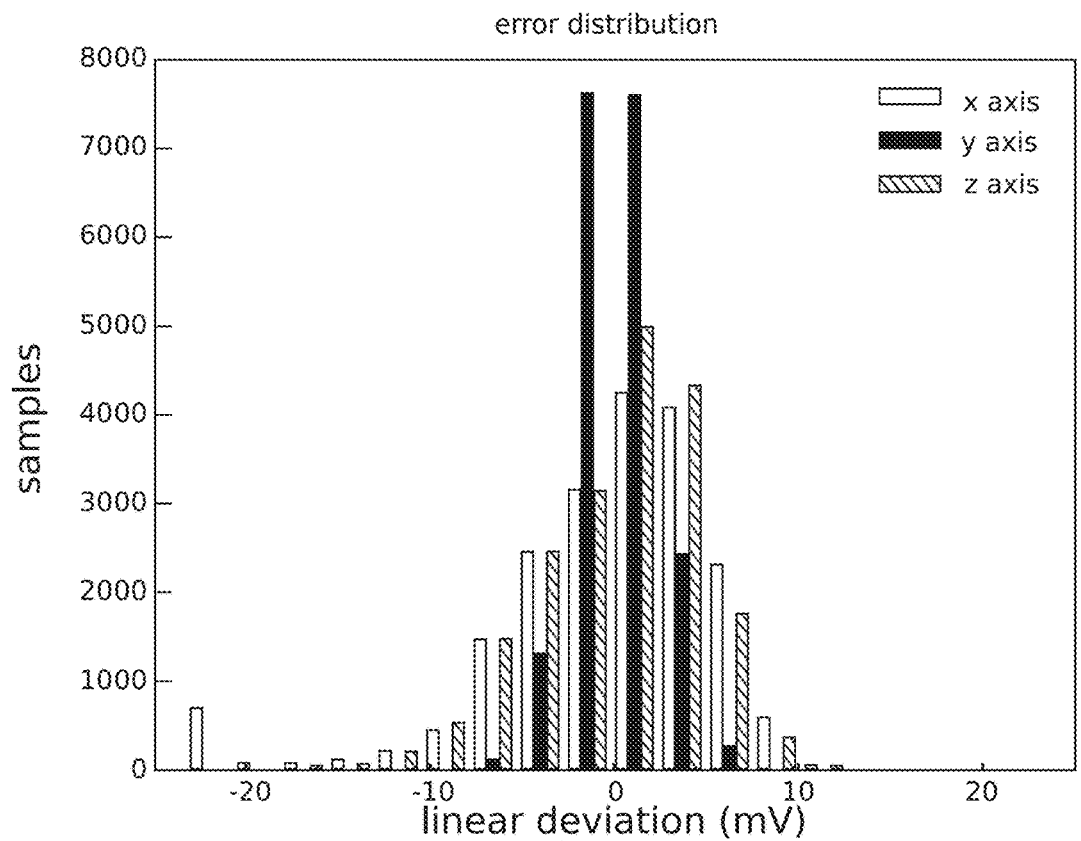
FIGS. 4A-4B show simulated distributions of voltage potential gradient linearity scores in a left atrial heart chamber, according to some embodiments.
Figure 4B:
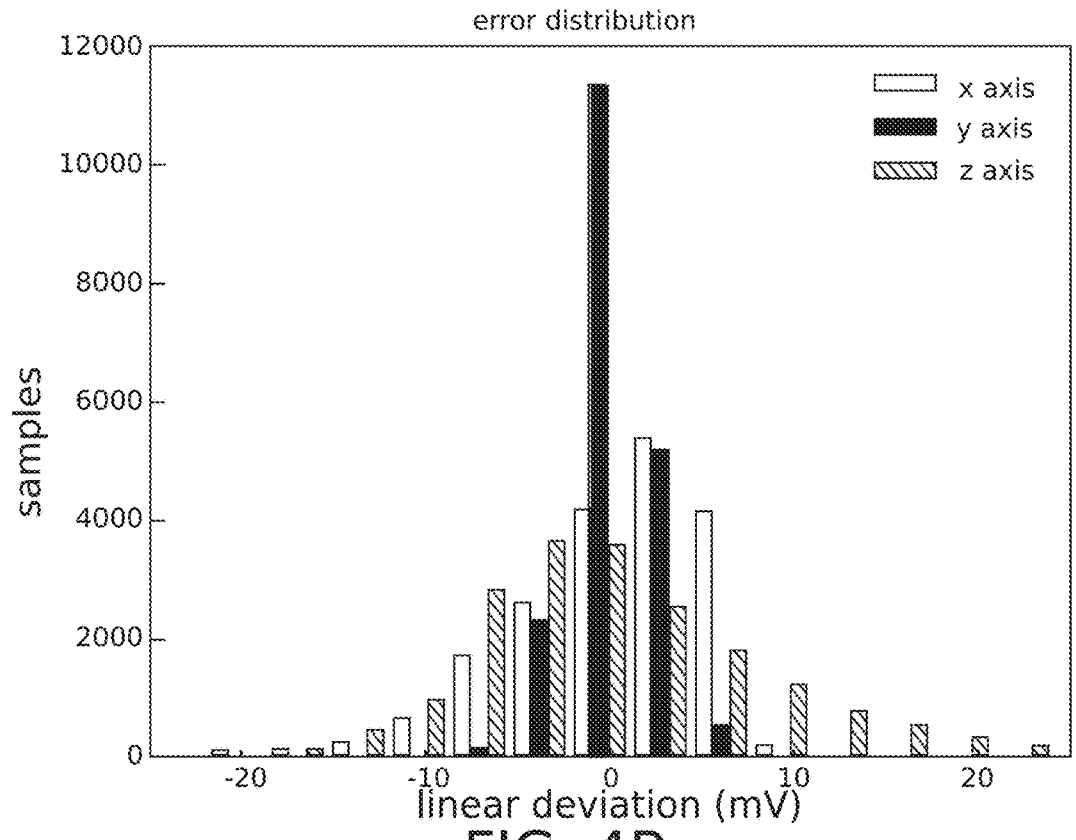

Reference is also made to FIGS. 4A-4B, which show simulated distributions of field potential gradient linearity scores in a left atrial heart chamber, according to some embodiments.

FIGS. 4A-4B show examples of distributions of linearity in the left atrium for two different body surface electrode configurations. Optionally, linearity is scored according to the characteristics of an error distribution (e.g., standard deviation) which represents the difference in millivolts from a best linear fit for each axis and at each sample point within a region of interest. It should be understood that a different criterion of potential gradient uniformity is optionally applied.

In the graphs shown, the X- and Y-axis linearity distributions are similar for each configuration, but there is a substantial difference for the Z-axis distributions, which are relatively spread out in FIG. 4B compared to FIG. 4A.

Reference is now made to Table 1 and Table 2, which give overall score results for two different configurations (A and B) in two different heart chambers (left and right atria).

TABLE 1

Left Atrium Scores

|  | CONFIGURATION A | CONFIGURATION B |
| --- | --- | --- |
| RANGE SCORE (V) | 0.35 | 0.1 |
| LINEARITY STD. DEV. (MV) | 7.7 | 6.1 |

TABLE 2

Right Atrium Scores

|  | CONFIGURATION A | CONFIGURATION B |
| --- | --- | --- |
| RANGE SCORE (V) | 0.3 | 0.2 |
| LINEARITY STD. DEV. (MV) | 7.8 | 4.6 |

It can be seen that Configuration B provides an increased linearity but smaller dynamic range compared to Configuration A in both heart chambers. Optionally, a choice from among the two configurations is made by a weighting function (for example, linearity is weighted more heavily than range, or vice versa). Optionally, the weighting function is linear. Optionally, the weighting function comprises a non-linearity such as a threshold. For example, if a dynamic range score of at least 0.3 V is considered to be a requirement for accurate navigation, then no weight is assigned to a configuration which cannot achieve this.

Figure 5:
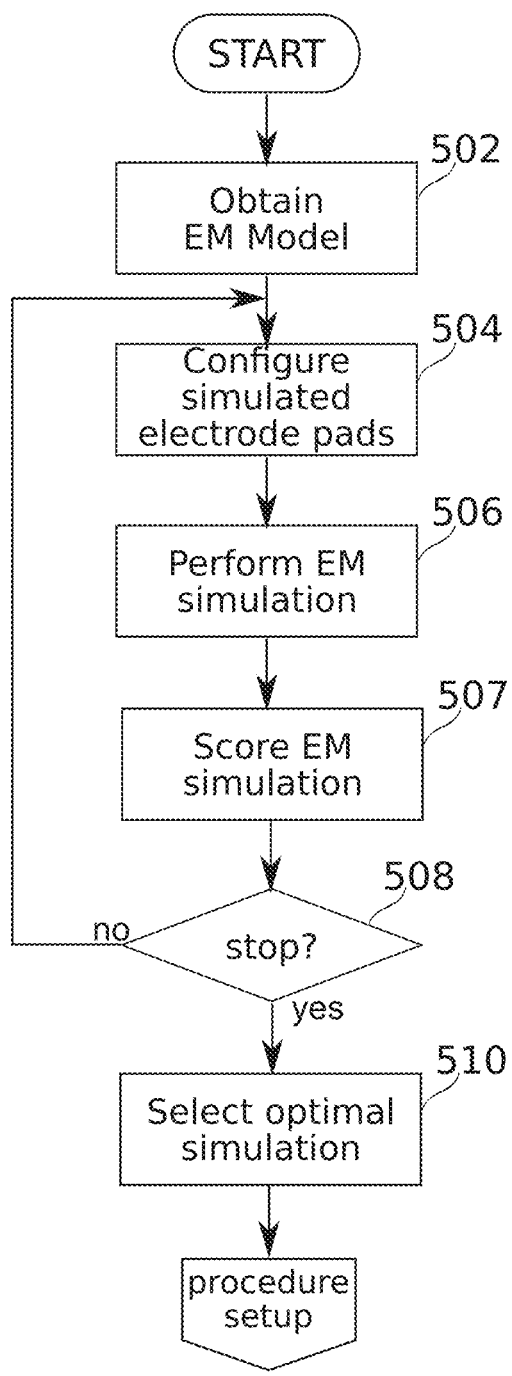
FIG. 5 schematically represents a method of pre-planning to select a body surface body surface electrode configuration for a procedure using intra-body electrical field sensing, according to some embodiments.

Method of Electrode Pad Placement Planning Using Electromagnetic Field Simulation Reference is now made to FIG. 5, which schematically represents a method of pre-planning to select a body surface electrode configuration for a procedure using intra-body electrical field sensing, according to some embodiments.

At block 502, in some embodiments, at least one electromagnetic simulation (EM simulation) corresponding to a patient is obtained. The model optionally comprises an anatomical description with dielectric properties (an electrical impedance model) described corresponding to tissue type at different anatomical regions.

In some embodiments, an EM simulation is generated de novo from the anatomical data of the patient. In some embodiments, the EM simulation is selected from a bank of models corresponding to different human body types. An exemplary bank of models is the commercially available XCAT visual human data library, which provides the ability to model a large range of male and female body morphologies with different body mass indexes, characteristics for fat capacity, size of the bones, size of the lungs, etc. As an example of relevant differences among humans with normal cardiovascular structures: tall and thin men typically have more apically pointed hearts, while men with heavier builds may have a heart located lower down on the diaphragm, across the chest. In another example, the cardiothoracic ratio between patients is very variable. In some embodiments, age, height, weight and cardiothoracic ratio from X-ray provide enough information to build a simulated anatomy, for example, from the XCAT library. In some embodiments, EM simulation and/or matching to select an EM simulation is performed as a remote service; for example, patient parameters and/or anatomical data are uploaded to a server. After body type selection from a library, and/or simulation based on the anatomy of the patient, a suitable electrode configuration is generated, and returned to the origin of the request.

Optionally, an EM simulation is selected, for example, according to age, heart state, breathing state, physical condition, size, weight, sex, and/or according to other criteria. Optionally, a bank-selected model is adjusted to more closely fit the particular anatomical details of the patient, for example by geometrical morphing of tissue type boundaries to match those of patient 3-D imaging data. A potential advantage of using a type-selected EM simulation is reduced complexity and/or resources required for simulation setup, compared to a de novo model.

At block 504, in some embodiments, simulated body surface electrodes are configured. Optionally, configuration comprises selection of the position and/or size of body surface electrodes to be used. Optionally, the configuration is selected from a range of preconfigured options. Available options are optionally associated with a banked EM simulation from which the current patient model is derived. Optionally (after a first round of simulations is performed), the configuration comprises iterative modification of a previously selected condition, for example, a displacement or a resizing of one or more body surface electrodes. Modification is optionally performed according to a suitable algorithm for searching body surface electrode configuration parameter space, for example, gradient descent and/or searching through a parameter range of at intervals. Optionally, typical placements are used for some body surface electrodes (for example, X- and/or Y-axis electrodes), and simulation is performed just for relatively problematic and/or sensitive electrodes, such as Z-axis positioning body surface electrodes, and/or body surface electrodes used for another sensing application such as tissue lesion assessment.

At block 506, in some embodiments, electromagnetic simulation (EM simulation) using the EM simulation together with simulated body surface electrodes is performed, for example as described in relation to FIGS. 2A-2B. Optionally, some simulations are run as "crude" simulations (for example, at low resolution), in order to rule out particularly poor body surface electrode configurations. Additionally or alternatively, for example, as configuration parameters converge, at least some simulated conditions are evaluated as partially modified versions of one or more full simulations. For example, simulation results are evaluated from an interpolation between two full simulations run under conditions that bracket the current configuration.

At block 507, in some embodiments, the EM simulation results are scored. Optionally, scoring comprises evaluation for criteria applicable to the structure of the electromagnetic field, such as potential gradient uniformity and/or dynamic range, for example as described in relation to FIGS. 3A-4B and Tables 1-2 herein. More generally, reference to the structure of an electromagnetic field should be understood to encompass the distribution of magnitudes and/or directions of vector values of the electromagnetic field. Optionally, scoring includes validation of the simulation results, for example, against previously calculated results and/or to ensure that the simulation results are reasonable in view of some other set of one or more constraints.

At block 508, in some embodiments, an evaluation is made as to whether the procedure should continue with further simulations by returning to block 505. For example, if all of an initial set of body surface electrode configurations have been searched, the simulation series is stopped. Additionally or alternatively, searching is stopped when a stopping condition such as minimal change in EM simulation score is reached.

If there are no more simulations to run, the simulation phase ends. At block 510, in some embodiments, a body surface electrode placement configuration (one of those modeled and scored) is selected for use in an actual procedure. Generally, the selected configuration is the one which is optimal according to the scoring procedure of block 507. When workflow resumes, it is optionally with a setup procedure, for example as described in relation to FIG. 6.

Figure 6:
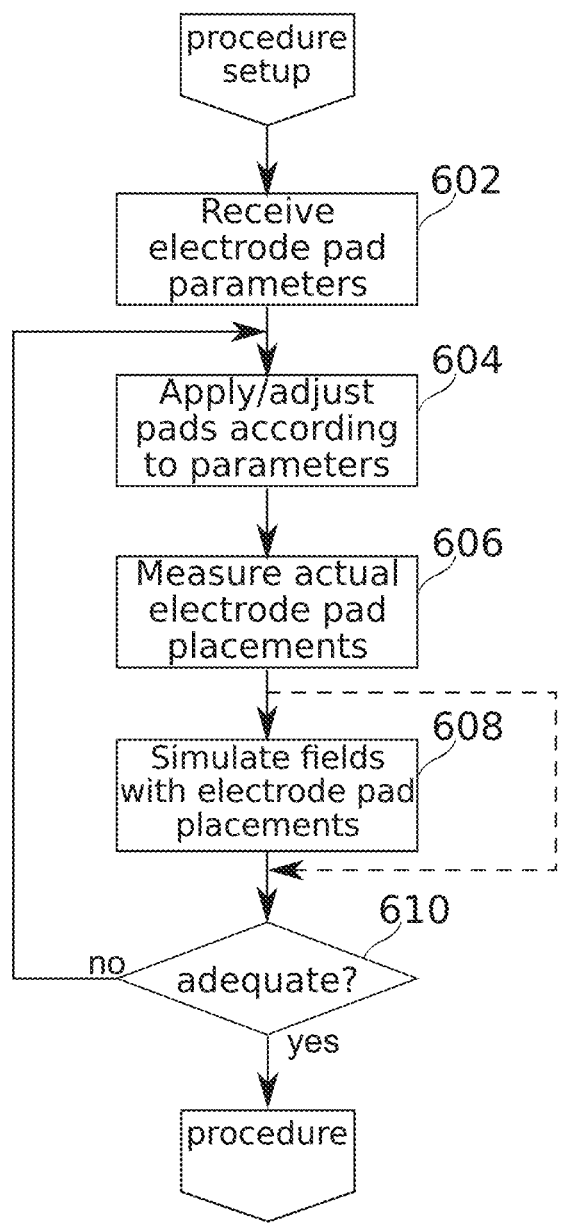
FIG. 6 schematically represents a method of setting up a body surface electrode configuration for a procedure using intra-body electrical field sensing, according to some embodiments.

Methods of Electrode Pad Placement and/or Electromagnetic Field Simulation Adjustment Reference is now made to FIG. 6, which schematically represents a method of setting up a body surface electrode configuration for a procedure using intra-body electrical field sensing, according to some embodiments.

At block 602, in some embodiments, the procedure begins, and body surface electrode configuration parameters are received. Optionally, the configuration parameters are defined by the parameters of the optimal electrode configuration selected in the procedure outlined in relation to FIG. 5. In some embodiments, the configuration is also associated with an EM simulation which is used in other aspects of the procedure (for example, in electrical field-guided intra-body navigation, tissue lesion assessment, or another procedure aspect).

At block 604, in some embodiments, body surface electrodes are placed. In a first iteration, the electrodes are placed according to the received configuration. After the first iteration, the electrodes may be placed according to other currently specified configuration parameters (for example, if new configuration parameters are provided from a simulation at block 608 or 610). Optionally, electrodes are placed with the assistance of fiducial marks, for example as described in relation to FIG. 7, herein.

At block 606, in some embodiments, the body surface electrode placements relative to the anatomy of the patient are measured. In some embodiments, for example, the measurement comprises optical photography of the body surface electrodes in situ. Optionally, the measurement comprises measuring body surface electrode positions relative to landmarks on the body. Optionally, the landmarks are fiducial marks placed previously (for example as described in relation to FIG. 7, herein). In some embodiments, the measurement of body surface electrode position relative to the anatomy of the patient is further registered to an anatomical model configured to simulate intra-body electrical fields. In some embodiments, measurement of the actual body surface electrode configuration comprises operating of the body surface electrodes to establish electrical properties such as the impedance between one or more electrode pairs.

Optionally at block 608, in some embodiments, electrical fields are simulated for the body surface electrode positions measured at block 606 (and optionally also for the actual electrical properties measured, such as actual impedance), based on the anatomical model and electrical field simulation; for example as described in relation to FIGS. 2A-2B. Optionally, this simulation is used as input to block 610 for deciding whether the electrode placement should be accepted. Optionally, this simulation is used to refine and/or replace the body surface electrode configuration parameters received at block 602. For example, further EM simulations are optionally performed for body surface electrode placements near to the current placement (e.g., near to may be spatially near, near in the sense of requiring adjustment of just one electrode, and/or near in the sense of assuming a different impedance of body surface electrode contact with skin).

At block 610, in some embodiments, adequacy of the body surface electrode placement of block 606 is evaluated. In some embodiments, evaluation of adequate placement comprises placement within a specified tolerance of a pre-planned position. For example, a body surface electrode is within a placement tolerance of 5 mm, 10 mm, 15 mm, or another greater, lesser, or intermediate distance from pre-planned position. In some embodiments, evaluation of adequate placement comprises evaluating if a simulated electrical field, simulated under conditions of the measured actual body surface electrode placements, produces electrical field properties satisfying criteria such as those used in pre-planning simulation. For example, simulated fields produced by the actual body surface electrode placement are found to have a field linearity score (or other criterion score) no less optimal than the planned body surface electrode placement, or than another preset value. Optionally, some degradation is allowed: for example, the criterion score is allowed to be degraded by up to 10%, 20%, 30%, or another larger, smaller, or intermediate degree of degradation. Optionally, additional simulations produced at block 608 are used as a basis for evaluating the adequacy of the current placement (e.g., to evaluate if a better "nearby" positioning can be suggested).

If the actual placement is considered to be adequate, the body surface electrode placement procedure ends, optionally continuing with the main catheter procedure itself. Optionally, if a new simulation was produced at block 608, electrode placement parameters associated with this simulation replace the parameters originally received at block 602. If placement is inadequate, the procedure optionally returns to block 604, at which body surface electrode positioning is adjusted.

Figure 7:
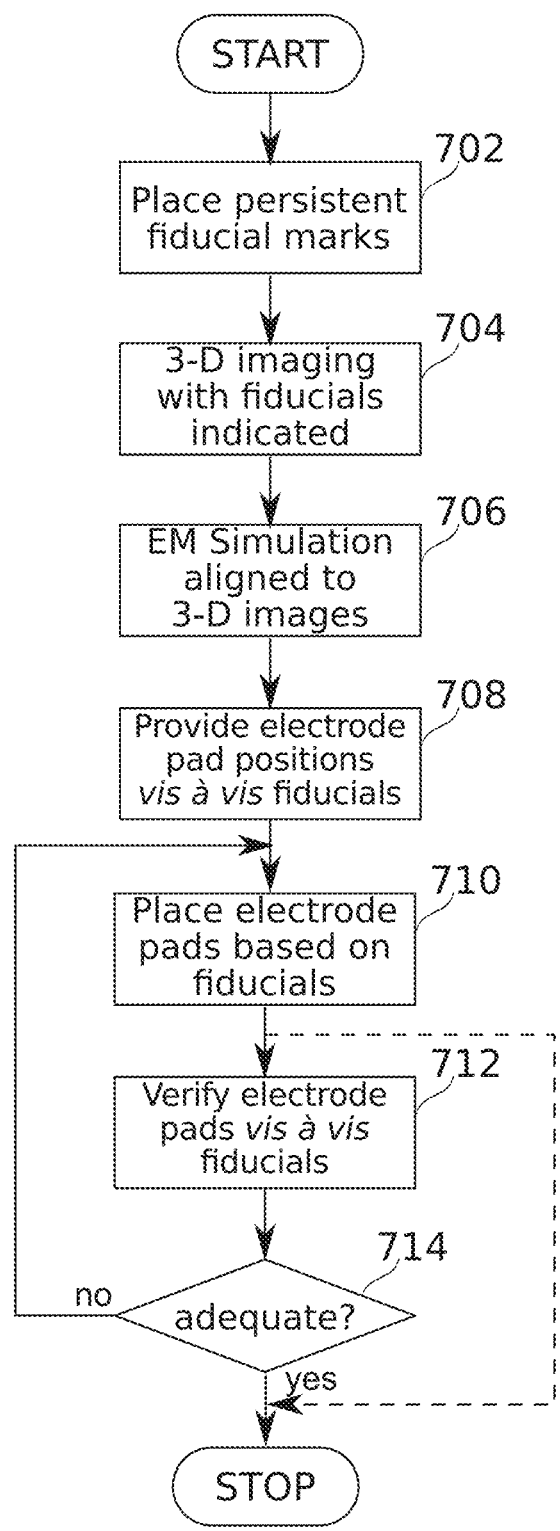
FIG. 7 schematically represents a method of using persistent fiducial marks to set up a body surface electrode configuration for a procedure using intra-body electrical field sensing, according to some embodiments.

Reference is now made to FIG. 7, which schematically represents a method of using persistent fiducial marks to set up a body surface electrode configuration for a procedure using intra-body electrical field sensing, according to some embodiments.

In some embodiments, the method described in relation to FIG. 6 is part of a larger procedure by means of which persistent fiducial marks are used to assist in achieving a sufficient alignment between simulated electrical fields and actual electrical fields produced intra-body. Operations of the blocks of FIG. 7 involving simulations, imaging, and/or image processing are optionally performed by the use of a computer processor; optionally operations are distributed among a plurality of processors; for example, a server machine and a portable device such as a cell phone, tablet, and/or laptop.

At block 702, in some embodiments, persistent fiducial marks are placed on the body surface of a patient. The fiducial marks are placed, for example, as described in relation to FIG. 9A, herein. Examples of fiducial mark embodiments are also described in relation to FIG. 9B. Optionally, the fiducial marks on the patient body surface are "persistent", at least in the sense that they persist between an initial 3-D anatomical imaging session (for example, CT), and a later session where the fiducial marks are used to align a simulated electrical field to the patient anatomy during intra-body probe sensing, for example, for electrical field-guided navigation and/or lesion assessment. Optionally, instead of or in addition to placing exogenous fiducial marks, the native appearance of the patient's skin surface (including, for example, distinguishing areas of skin coloration and/or shape) is recorded relative to temporary fiducial marks. Distinctive regions of the native skin surface are thereafter treated as persistent fiducial marks.

At block 704, in some embodiments, 3-D imaging is performed (for example, by CT or MRI), wherein the persistent fiducial mark positions are included in the 3-D imaging data. Optionally, this is by the persistent fiducial marks themselves being visible under the imaging methodology used. Optionally, temporary fiducial marks (visible in the selected 3-D imaging modality) are in position at the region of the persistent fiducial mark during imaging. Optionally, the temporary fiducial marks are in position at other locations, but with a relationship to the persistent fiducial marks such that the locations of the persistent fiducial marks can be calculated based on the temporary marks. It should be noted that fiducial marks used in 3-D imaging are often relatively large and obtrusive, so that they are not suitable for extended attachment to a body. However, fiducial marks used for the present method are optionally sufficiently small and/or flat that they can be worn for an extended period without significant discomfort.

At block 706, in some embodiments, one or more simulated electromagnetic fields are generated, based at least in part on the anatomical data obtained at block 704. The simulation (EM simulation) is performed, for example, as described in relation to FIG. 5, herein.

At block 708, in some embodiments, body surface electrode positions (for example, as calculated in the method of FIG. 5) are provided in an instruction format that describes positions relative to the persistent fiducial marks (optionally, this is a particular embodiment of how electrode parameters are provided at block 602 of FIG. 6). The format can comprise, for example, a demonstration movie, a physical template, written/graphical instructions, and/or an augmented reality display (display of an overlay indicating target body surface electrode position on a live image). Examples of such formats are also described in relation to FIGS. 9A-9B.

At block 710, in some embodiments, the body surface electrodes are placed, based on the instructions provided at block 708. In some embodiments, placement of the electrodes comprises a first step of visually aligning the electrode to a particular position which it should cover (e.g., visualized through a window comprising a hole, cutaway, and/or grating in the electrode itself), and then a second step of exposing adhering material around the visualizing window so that the electrode can be firmly secured.

At block 712, in some embodiments, body surface electrode positions are verified. In some embodiments, augmented reality positioning provides live feedback about positioning, such that it is immediately apparent to an operator using the feedback if a body surface electrode is in a correct position or not. In some embodiments, photography is otherwise used to verify body surface electrode position relative to fiducial marks or other landmarks (e.g., feedback is given as an offline result, rather than shown on a live display). Potentially, however, there are exigencies at the time of body surface electrode placement that interfere with placement as planned; for example, skin condition, placement of other leads and/or equipment, and/or availability of the planned size and/or shape of electrodes in clinical stores. In some embodiments, verification comprises sending electrical signals through body surface electrodes, which are optionally confirmed (in block 714) as sufficiently or insufficiently corresponding to those predicted by the electromagnetic simulation.

At block 714, in some embodiments, a determination is made as to whether or not body surface electrode placement is adequate, for example, as described in relation to block 610 of FIG. 6. Optionally, results are indicated to an operator (for example, on a screen display, and/or by another alert method). Optionally, if positioning is inadequate, the procedure returns to block 710 for adjustment. Preferably, adjustment continues until positioning is accurate to within resolution of no more than about 10 mm. In some embodiments, the final placement of the body surface electrodes is used in the generation of a final EM simulation (optionally either de novo or by adjusting the current EM simulation).

Examples of Electrode Pad Placement

Figures 8A, 8B:
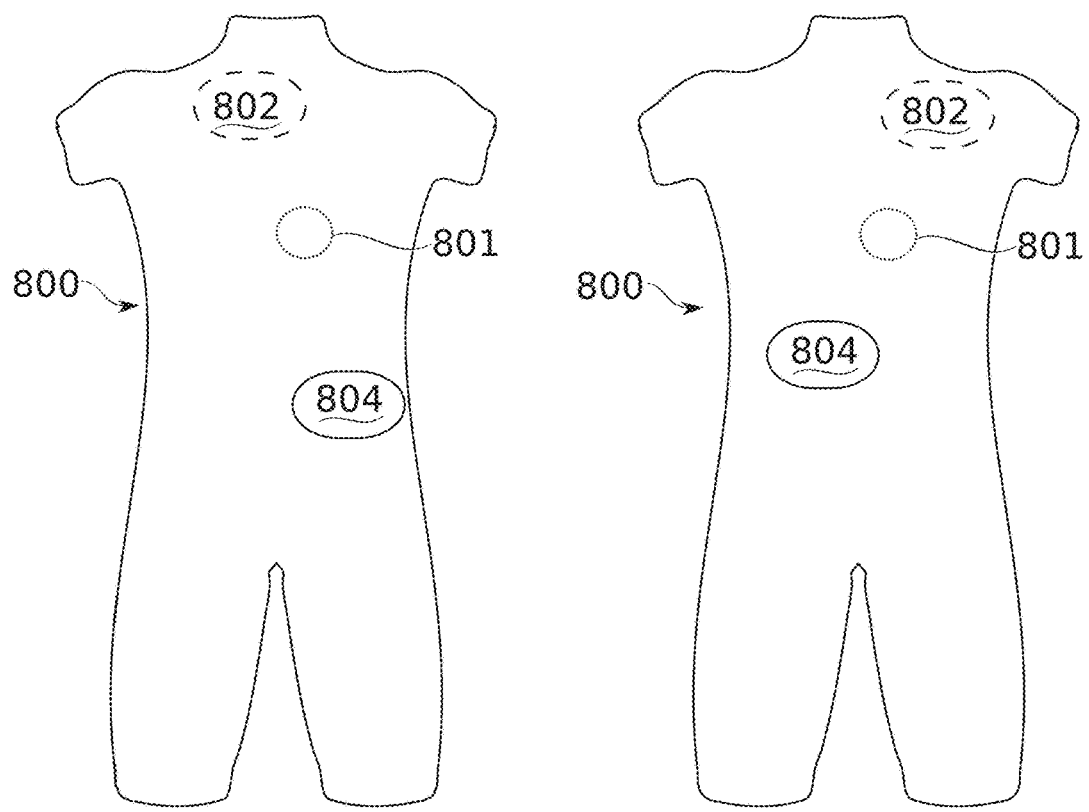
FIGS. 8A, 8B and 8C schematically illustrates placement of Z-axis body surface electrodes, on a body, according to some embodiments.
Figure 8C:
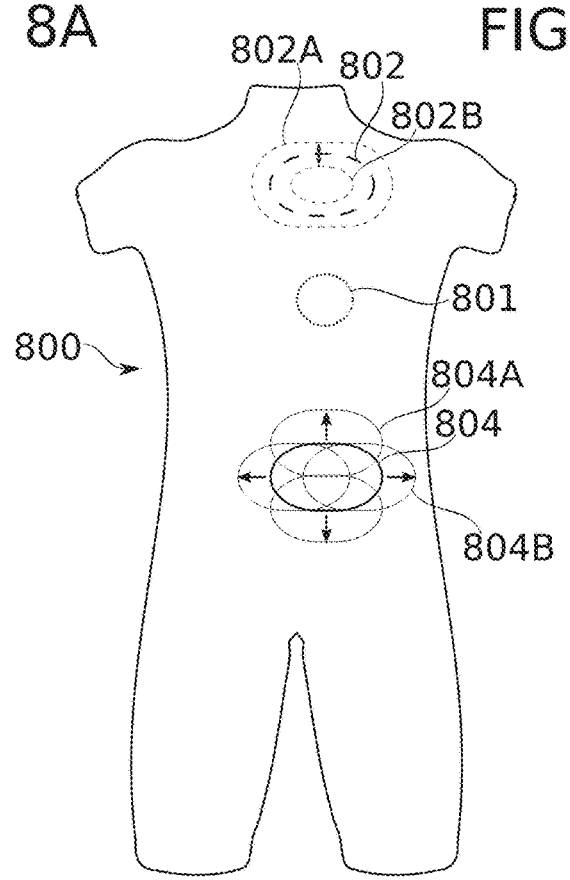

Reference is now made to FIGS. 8A-8C, which schematically illustrates placement of Z-axis body surface electrodes 802, 804 on a body 800, according to some embodiments.

In some embodiments, body surface electrodes 802, 804 define a Z-axis electrical field through a region of interest 801 (for example, the heart). Optionally, the body surface electrodes 802, 804 are positioned depending, for example, on particulars of patient anatomy. As shown, body surface electrode 802 is on the back (dorsal side), while body surface electrode 804 is on the front (ventral side). FIGS. 8A-8C schematically illustrate three different (non-exhaustive) general options: back-right shoulder/front-lower-left abdomen, back-left shoulder/front-mid-right abdomen, and center-back/front-lower-center abdomen, respectively. Optionally, front/back are inverted. Optionally (and as illustrated), the area of interest 801 is slightly offset from center, and body surface electrode placements are optionally offset likewise.

Due, for example, to individual variations in anatomy, it is not necessarily known without further investigation which general body surface electrode configuration provides the most nearly optimal field conditions in the region of interest. Optionally, EM simulations (for example, as described with respect to FIGS. 2A-2B) are used to determine which configuration is preferred.

Optionally, further refinements in body surface electrode position are made as a result of EM simulation. FIG. 8C shows examples of optional variations in size for body surface electrode 802 in the form of larger body surface electrode 802A, and smaller body surface electrode 802B. Variation can be accomplished, for example, by selection from a range of standard sizes, and/or by trimming of a body surface electrode. FIG. 8C also shows various offsets for body surface electrode 804, for example, offset positions 804A and 804B. It is to be understood that offsets can be in any direction, and optionally combined with adjustments in body surface electrode size.

Figure 9A:
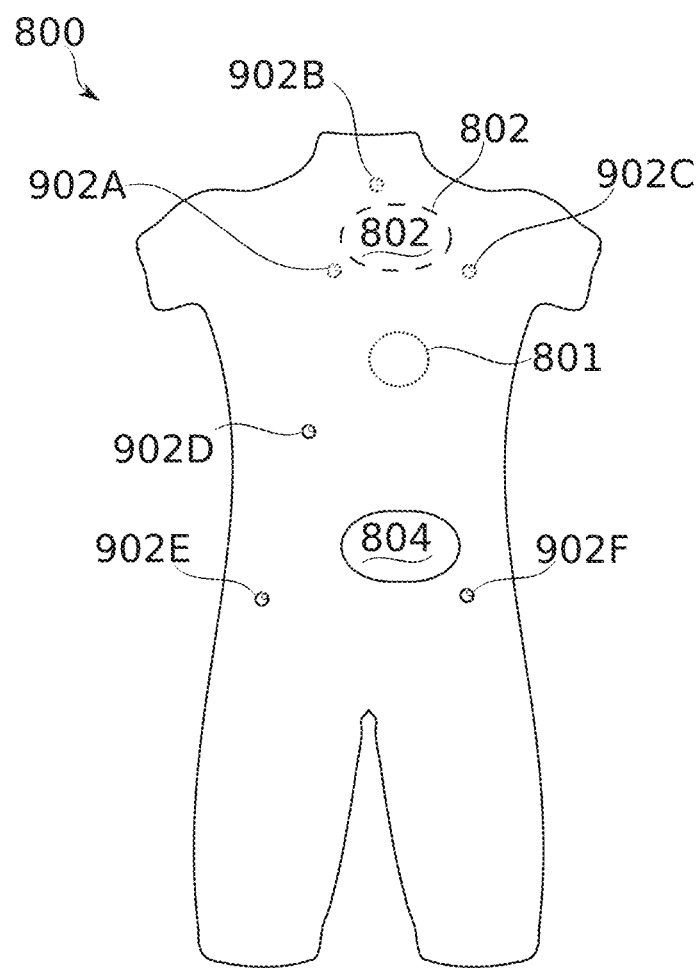
FIG. 9A shows the relationship of body surface electrode placement fiducial marks with body surface electrodes, according to some embodiments.
Figure 9B:
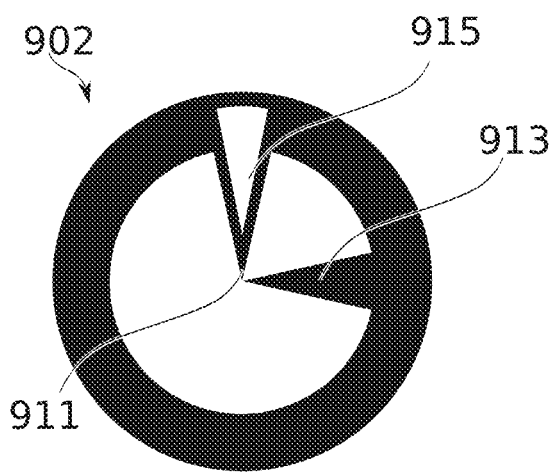
FIG. 9B shows an example of a shape for a fiducial mark, according to some embodiments.

Reference is now made to FIG. 9A, which shows the relationship of body surface electrode placement fiducial marks 902A, 902B, 902C, 902D, 902E, and 902F with body surface electrodes 802, 804, according to some embodiments. Reference is also made to FIG. 9B, which shows an example of a shape for a fiducial mark 902, according to some embodiments.

In some embodiments of the invention, fiducial marks 902A-902F are used to assist in the positioning of body surface electrodes 802, 804 in preparation for the generation of intra-body electrical fields used in intra-body field sensing. Electrical field-guided intra-body navigation in particular potentially benefits from strict registration between a simulated (or otherwise predicted) intra-body electrical field, and the actual intra-body electrical field which is produced. A method of achieving this is described, for example, in relation to FIG. 7, herein.

In some embodiments, groups of fiducial marks such as 902A-902C and/or 902D-902F are placed on a body in the course of measurements made to obtain anatomical information about the patient (for example, 3-D imaging such as CT or MRI). Optionally, the marks are placed as a group (for example, the back-located group of fiducial marks 902A-902C) which roughly surrounds a limited region where experience suggests that the body surface electrode 802 is likely to be located for the eventual invasive procedure. Optionally, a looser grouping is used (such as shown for front-located group of fiducial marks 902D-902F). Where feasible, it is a potential advantage for fiducial marks to be located so that the final body surface electrode positions are likely to be close by, to reduce the magnitude of measurement error.

In some embodiments, a fiducial mark comprises a marking which can potentially persist for days or weeks on the patient body. The fiducial marking comprises, for example, a temporary "tattoo", which can comprise, for example, an applique, peel-off sticker, ink marking, injected marker, electronic identification component, and/or another form of marker. In some embodiments, the marking includes features to assist in clearly indicating position; for example, fiducial mark 902 comprises two distinctly shaped pointers 915, 913, which converge to indicate a central reference region 911. Distinct shaping allows clear marking of direction, as well as of position.

In some embodiments, body surface electrode placement is performed according to instructions expressed in terms of the fiducial mark positions and/or orientations. Optionally, the instructions are textual and/or graphical; for example, printed and/or displayed on a screen. Optionally the instructions comprise a measuring template, for example, a printed template, which can be physically aligned to two or more of the fiducial marks 902A-902F to indicate where a body surface electrode 802, 804 should be placed. Optionally, the body surface electrode 802, 804 is temporarily attached to the template so that placement of the template itself comprises placement of the body surface electrode 802, 804. Optionally, the instructions comprise indications in an "augmented reality" display. For example, target body surface electrode positions are superimposed on a live optical image of the patient's body, where the alignment is made relative to fiducial marks also visible in the live optical image. The live optical image and positioning indication are performed, for example, using a position-sensitive head-mounted display, a hand-held integrated camera and display (such as a computerized cell phone or tablet), or another means of integrating optical data, position information, and the calculated target piston of a body surface electrode.

Reference is now made to FIGS. 10A-10E, which illustrate examples of different electrode configurations 1010, 1020, 1030, 1040, 1050 on the body surface of a pig 100, according to some exemplary embodiments of the invention.

Shown are examples of electrodes of different size, shape, and/or relative placement, viewed from the ventral surface of a pig. In electrode configuration 1010 of FIG. 10A, left and right electrodes 1014 and 1012 are shown in different rectangular sizes, located under the forelimb shoulders of the animal. A relatively large chest electrode 1016 is shown, while abdominal electrode 1018 is relatively small. This would tend to favor a low impedance for electrode 1016, which is a potential advantage, for example, for making dielectric property measurements of tissues near the heart. However, electrical fields generated using relatively small square electrodes such as 1018 are typically less uniform.

Figures 10A, 10B, 10C:
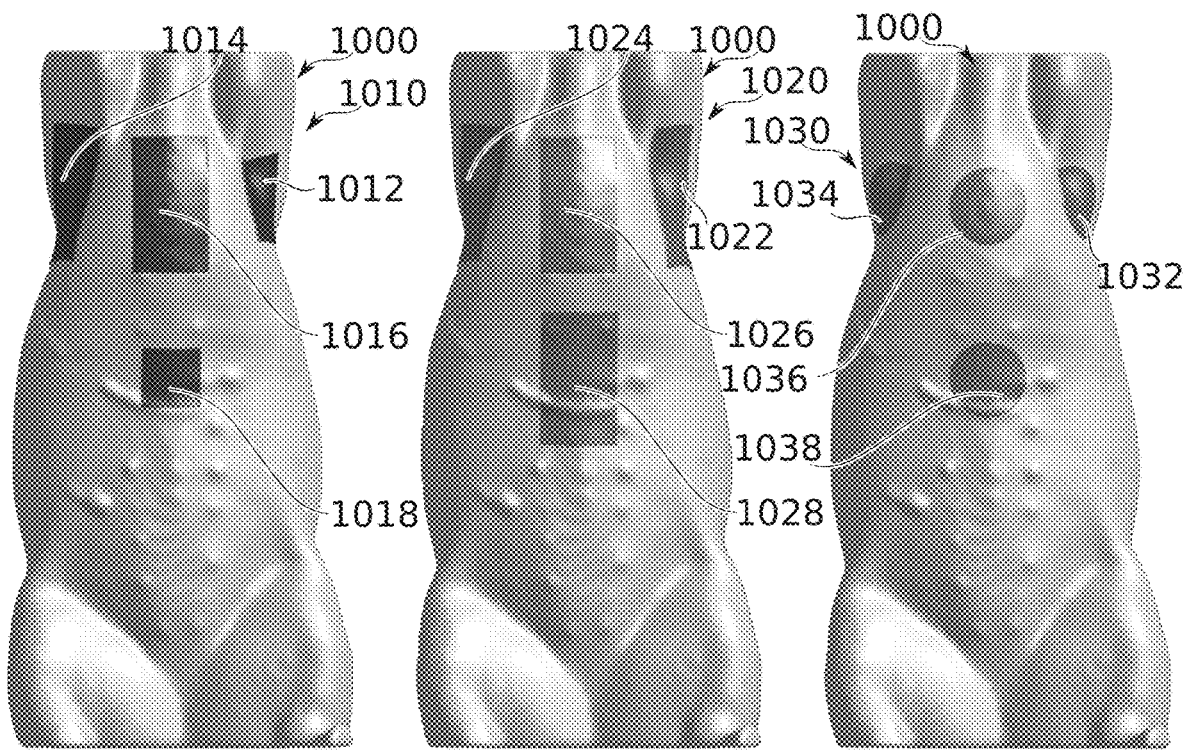
FIGS. 10A, 10B, 10C, 10D and 10E illustrate examples of different electrode configurations on the body surface of a pig, according to some embodiments.

In electrode configuration 1020 of FIG. 10B, larger rectangular pads 1022, 1024, 1026, and 1028 are used in all positions, tending to invert the relative potential advantages and/or disadvantages of configuration 1010.

Electrode configuration 1030 of FIG. 10C uses round electrodes 1032, 1034, 1036, 1038 in the same placement positions. Although smaller (and thus having a tendency to focus the field lines near the electrodes), the cornerless design potentially removes a source of electrical field anisotropy. Electrode configuration 1040 of FIG. 10D uses the same electrode design for electrodes 1042, 1044, 1046, 1048; but with abdominal electrode 1048 placed lower than corresponding electrode 1038. This potentially tends to make the electrical field lines running near the heart more nearly isotropic (since they are more distant from the electrode source), but at the cost of decreasing field strength.

Figures 10D, 10E:
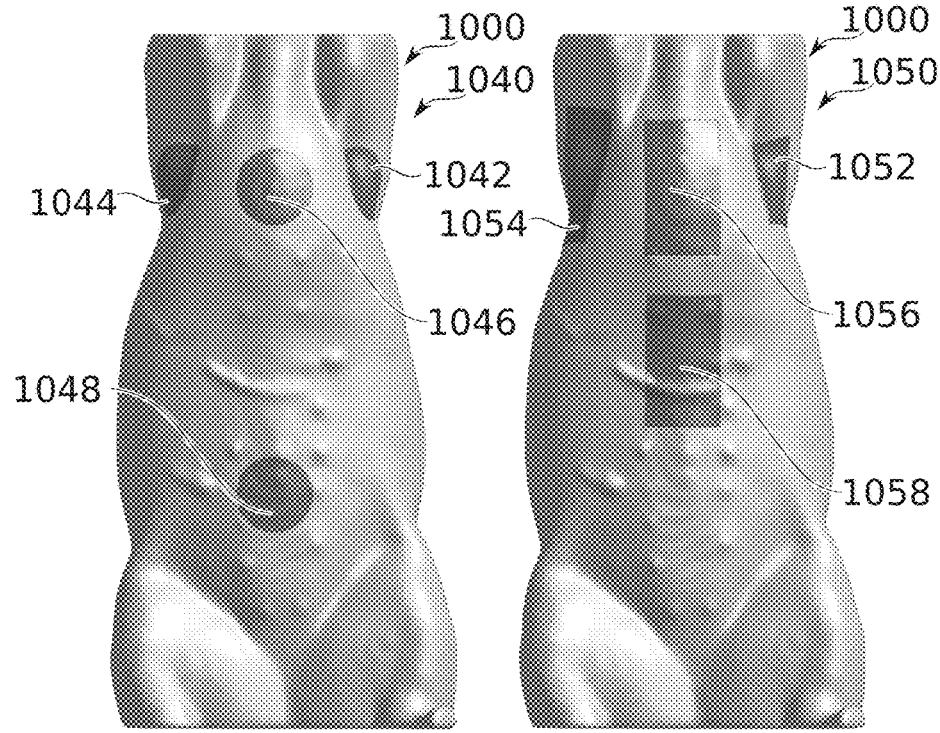

Finally, electrode configuration 1050 of FIG. 10E is a mix of configurations 1010 and 1020; with electrodes 1054, 1052, and 1056 sized and placed like those of configuration 1010, but with abdominal electrode 1058 being of the same placement and large design as electrode 1028 of FIG. 10B. Potentially, this results in a compromise between the relative potential advantages and disadvantages of configurations 1010 and 1020.

It should be noted, in comparison to the simulation configuration of FIGS. 1B-1C, that the electrodes are shown conforming to the body surface of the animal, even in locations where the surface is convoluted (e.g., under the forearm shoulders). This is advantageously implemented as a feature of the simulation itself, potentially resulting in more realistic structure of the simulated field, compared to the block-like electrodes of FIGS. 1B-1C. In some embodiments electrodes are electrically simulated as an equipotential surface. Optionally, electrode simulation takes into account structure and internal electrical properties (such as resistivity) of the electrode itself, allowing simulation of voltage variations across the surface of the electrode.

In some embodiments, the simulation is further augmented to include simulation of the conductive properties of a gel or other electrolyte layer, positioned between the electrode itself and the skin. In some embodiments, an electrode gel layer is specified, for example, to have a thickness of about 0.8 mm. Optionally another thickness of the gel layer is specified; for example: about 0.4 mm, 0.6 mm, 1.0 m, 1.2 mm, or another larger, smaller, or intermediate thickness. In some embodiments, a resistivity of a gel layer is specified with a resistivity, for example, of about 1500 Ω·cm. Optionally another resistivity of the gel layer is specified; for example: about 1000 Ω·cm, about 1250 Ω·cm, about 1750 Ω·cm, about 2000 Ω·cm, or another larger, smaller, or intermediate resistivity.

Reference is now made to FIGS. 1A-11B, which each represent navigational resolution for four different electrode configurations, according to some exemplary embodiments of the invention.

In each figure, four overlaid segmentations of the same porcine atrium (left atrium in FIG. 11A; right atrium in FIG. 11B) and associated blood vessels are shown. The four segmentations are scaled according to the millivolts per centimeter which simulation predicts at the different positions within the segmentation, as a result of the use of four different body surface electrode configurations. Larger scaling thus reflects the availability of higher navigational resolution, and is preferred.

Figure 11A:
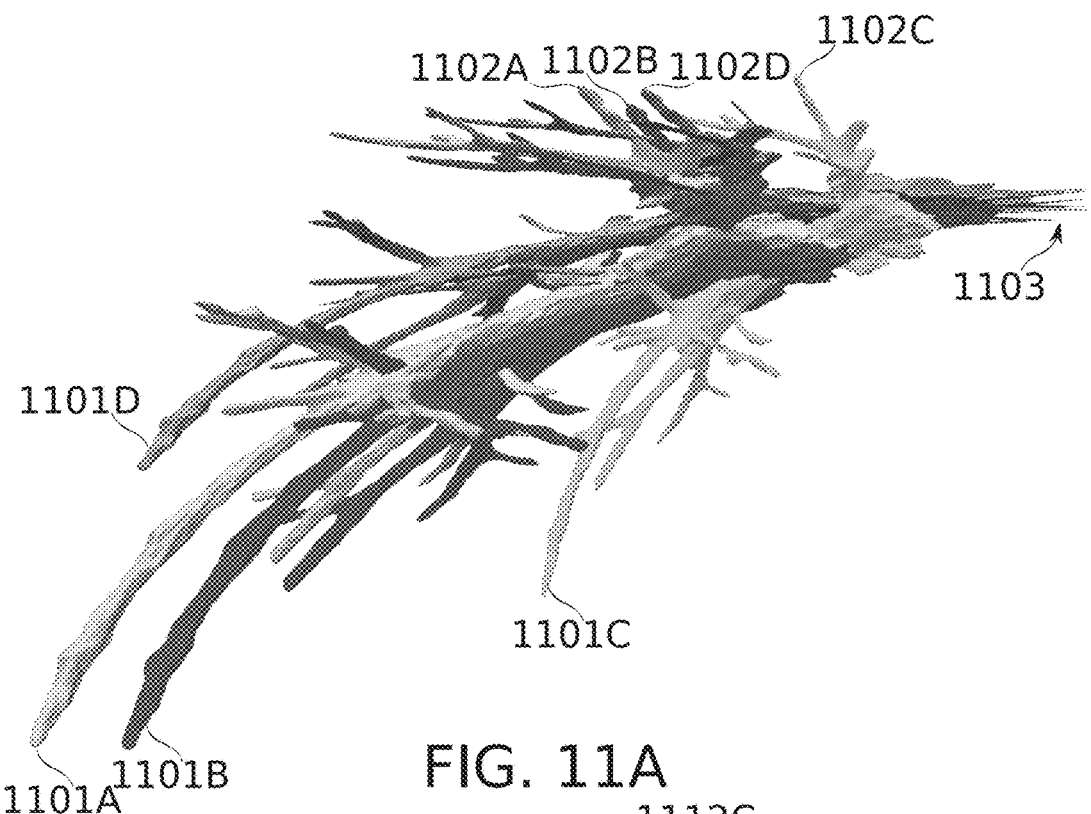
FIGS. 11A-11B each represent navigational resolution for four different electrode configurations, according to some embodiments.
Figure 11B:
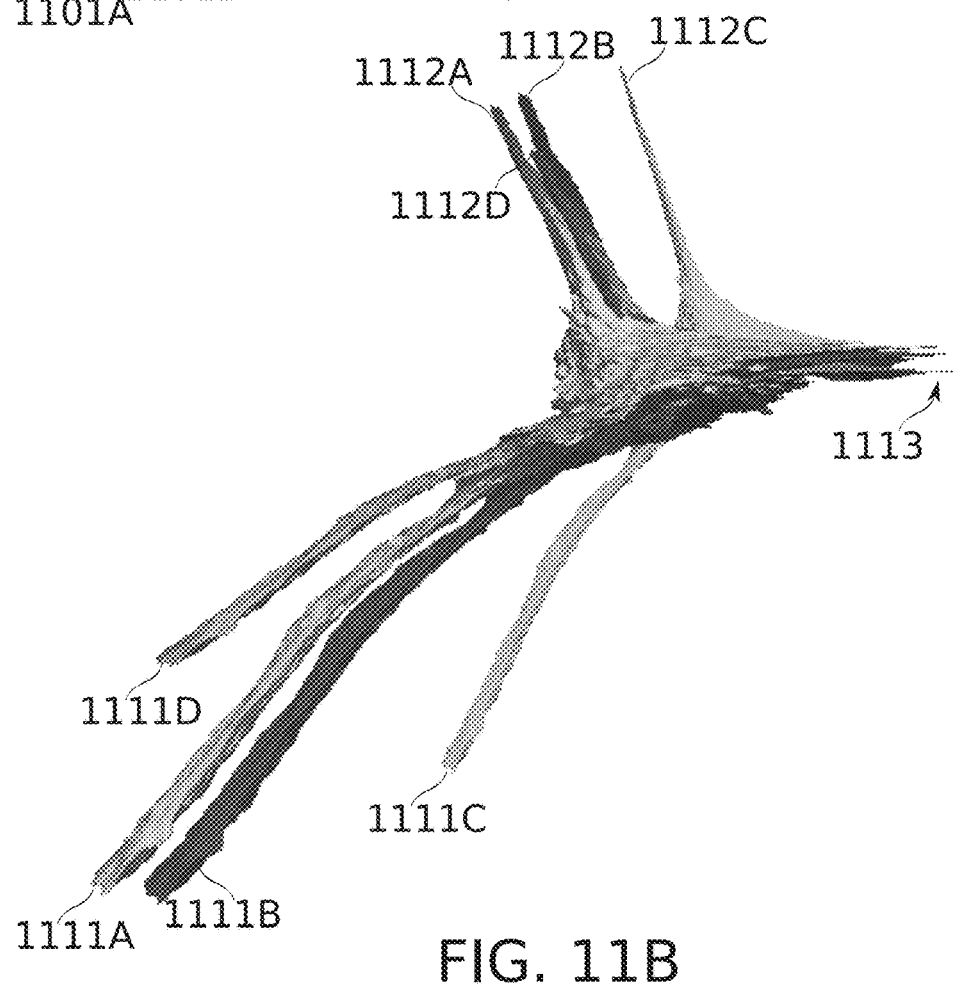

All four segmentations are aligned at region 1103 (FIG. 11A) or region 1113 (FIG. 11B). To assist in distinguishing the various shades of gray by which different segmentations are indicated, a few landmarks are correspondingly marked as well. In FIG. 11A, vascular branches 1102A-1102D are all corresponding, as are vascular branches 1101A-1101D. In FIG. 11B, vascular branches 1112A-1112D are all corresponding, as are vascular branches 1111A-1111D. Branches marked with the same letter in the same figure belong to the same segmentation. In FIG. 11A, the segmentation comprising landmarks 1101D and 1102D was generated using a default body surface electrode configuration. Larger body surface electrodes in new positions for one axis were used to generate the electrical field used in scaling the segmentation comprising landmarks 1101B and 1102B. The scaled segmentation is correspondingly larger in one dimension (height, in the view shown).

In the simulation which scales the segmentation comprising landmarks 1101A, 1102A, a further substitution was made, using larger pads for the X-axis (horizontal width, in the view shown). This turned out to be the optimal configuration of those tested, for providing the highest resolution for navigation. A forth body surface electrode configuration comprising landmarks 1101C, 1102C used round electrodes in the same positions as for the segmentation comprising landmarks 1101A, 1102A; but was found to be significantly poorer in X-axis resolution than any of the alternatives.

The same descriptions apply also to FIG. 11B, changed as necessary to indicate the corresponding landmarks of FIG. 11B (landmark 1111A instead of 1101A; landmark 1112D instead of 1102D, etc.).

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used to herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of placing body surface electrodes on a patient, the method comprising:
   placing the body surface electrodes on the patient in a first placement configuration;
   obtaining data related to the body surface electrodes;
   simulating electrical fields expected to be induced by the body surface electrodes placed on the body surface in the first placement configuration based, in part, on the data;
   determining whether the placement of the electrodes is inadequate based on the electrical fields simulated; and
   changing the placement of the body surface electrodes on the patient based on the determining of an inadequate placement.

2. The method of claim 1, wherein the determining comprises generating an adequacy score of the simulated electrical fields.

3. The method of claim 2, wherein the determining comprises comparing the adequacy score of the simulated electrical fields to the adequacy score of at least one other set of simulated electrical fields.

4. The method of claim 3, wherein the at least one other set of simulated electrical fields includes electrical fields simulated according to a planned electrode placement configuration.

5. The method of claim 2, wherein the adequacy score is evaluated based on at least one of voltage potential gradient uniformity and voltage potential gradient dynamic range.

6. The method of claim 2, wherein the adequacy score is evaluated based on distribution of at least one of electromagnetic field vector values and electromagnetic field magnitudes.

7. The method of claim 2, wherein the adequacy score is evaluated based on validation of the simulated electrical fields compared to previously calculated results.

8. The method of claim 2, wherein the adequacy score is evaluated based on ensuring that the simulated electrical fields satisfy a set of one or more constraints.

9. The method of claim 1, wherein the simulating electrical fields comprises evaluating electromagnetic field equations for elements within an impedance model.

10. The method of claim 1, wherein the simulating comprises interpolation between a plurality of electrical field simulations.

11. The method of claim 1, wherein obtaining the data comprises operating the body surface electrodes to obtain a measurement of at least one electrical property of the patient.

12. A system for instructing placement of placing body surface electrodes on a patient, the system comprising a processor configured to:
    receive data related to an actual first placement configuration of body surface electrodes on the patient in a first placement configuration;
    simulate electrical fields expected to be induced by the body surface electrodes placed on the body surface in the first placement configuration based, in part, on the data;
    determine whether the placement of the electrodes is inadequate based on the electrical fields simulated; and
    indicate a change in the placement is needed, based on the determining of an inadequate placement.

13. The system of claim 12, wherein the processor is configured to simulate electrical fields by evaluation of electromagnetic field equations for elements within an impedance model.

14. The system of claim 12, wherein the processor simulates the electrical fields within a region of a heart.

15. The system of claim 14, wherein the region of the heart comprises an atrium.

16. The system of claim 12, wherein the processor is configured to operate the body surface electrodes to create measurements of at least one electrical property of the patient, and the data comprises the created measurements.

17. The system of claim 16, wherein the at least one electrical property comprises an impedance between one or more pairs of the surface.

* * * * *